United States Patent
Luckhurst et al.

(10) Patent No.: US 7,517,989 B2
(45) Date of Patent: Apr. 14, 2009

(54) PIPERIDINE DERIVATIVES USEFUL AS MODULATORS OF CHEMOKINE RECEPTOR ACTIVITY

(75) Inventors: Christopher Luckhurst, Loughborough (GB); Matthew Perry, Loughborough (GB); Hitesh Sanganee, Loughborough (GB); Brian Springthorpe, Loughborough (GB)

(73) Assignee: AstraZeneca AB (SE)

( * ) Notice: Subject to any disclaimer, the term of this patent is extended or adjusted under 35 U.S.C. 154(b) by 648 days.

(21) Appl. No.: 10/508,331

(22) PCT Filed: Mar. 17, 2003

(86) PCT No.: PCT/SE03/00443

§ 371 (c)(1), (2), (4) Date: Sep. 17, 2004

(87) PCT Pub. No.: WO03/078395

PCT Pub. Date: Sep. 25, 2003

(65) Prior Publication Data

US 2005/0176708 A1    Aug. 11, 2005

(30) Foreign Application Priority Data

Mar. 19, 2002    (SE) ..................... 0200844

(51) Int. Cl.
C07D 211/00 (2006.01)
C07D 295/00 (2006.01)

(52) U.S. Cl. ...................... 546/184; 546/186

(58) Field of Classification Search .............. 546/184, 546/186
See application file for complete search history.

(56) References Cited

U.S. PATENT DOCUMENTS

| | | | |
|---|---|---|---|
| 4,588,722 A | 5/1986 | Janssens et al. | |
| 4,695,575 A | 9/1987 | Janssens et al. | |
| 5,883,096 A | 3/1999 | Lowe et al. | |
| 5,889,006 A | 3/1999 | Lowe et al. | |
| 5,952,349 A | 9/1999 | Asberom et al. | |
| 5,977,138 A | 11/1999 | Wang et al. | |
| 6,066,636 A | 5/2000 | Kozlowski et al. | |
| 6,294,554 B1 | 9/2001 | Clader et al. | |
| 6,387,930 B1 | 5/2002 | Baroudy et al. | |
| 6,440,440 B1 | 8/2002 | Meerpoel et al. | |
| 6,525,070 B2 | 2/2003 | Rigby et al. | |
| 6,759,411 B2 | 7/2004 | Ko et al. | |
| 6,903,115 B2 | 6/2005 | Rigby et al. | |
| 7,179,922 B2 | 2/2007 | Lawrence et al. | |
| 7,186,718 B2 | 3/2007 | Gustafsson et al. | |
| 7,238,691 B2 | 7/2007 | Sanganee et al. | |
| 7,238,811 B2 | 7/2007 | Rigby et al. | |
| 7,265,227 B2 * | 9/2007 | Evans et al. | 546/216 |
| 7,307,090 B2 | 12/2007 | Evans et al. | |
| 2005/0182094 A1 | 8/2005 | Sanganee et al. | |
| 2006/0040984 A1 * | 2/2006 | Luckhurst et al. | 514/316 |
| 2006/0264463 A1 | 11/2006 | Luckhurst et al. | |
| 2006/0281726 A1 | 12/2006 | Luckhurst et al. | |
| 2007/0032523 A1 | 2/2007 | Caffrey et al. | |
| 2007/0179297 A1 | 8/2007 | Lawrence et al. | |

FOREIGN PATENT DOCUMENTS

| | | |
|---|---|---|
| EP | 0 099 139 | 1/1984 |
| EP | 0 121 972 | 10/1984 |
| EP | 0 145 037 | 6/1985 |
| EP | 0 151 824 | 8/1985 |
| EP | 0 151 826 | 8/1985 |
| EP | 1 076 055 | 2/2001 |
| EP | 1 362 857 | 11/2003 |
| GB | 1250719 | 10/1971 |
| WO | WO 93/10091 A2 | 5/1993 |
| WO | WO 95/08535 A1 | 3/1995 |
| WO | WO 96/26196 | 8/1996 |
| WO | WO 96/34857 | 11/1996 |
| WO | WO 96/41631 A1 | 12/1996 |
| WO | WO 97/24324 | 7/1997 |
| WO | WO 98/01425 | 1/1998 |
| WO | WO 98/05291 | 2/1998 |
| WO | WO 98/05292 | 2/1998 |
| WO | WO 98/06697 | 2/1998 |
| WO | WO 98/11128 | 3/1998 |
| WO | WO 99/04794 | 2/1999 |
| WO | WO 99/37304 | 7/1999 |
| WO | WO 99/38514 | 8/1999 |
| WO | WO 99/51578 | 10/1999 |

(Continued)

OTHER PUBLICATIONS

Copending U.S. Appl. No. 10/528,477.*

(Continued)

*Primary Examiner*—Rei-tsang Shiao
*Assistant Examiner*—Susannah Chung
(74) *Attorney, Agent, or Firm*—Fish & Richardson P.C.

(57) ABSTRACT

The present invention provides a compound of formula (I), wherein: Z is (A) OR (B) and wherein the remaining variables are defined herein; to a process for preparing such a compound; and to the use of such a compound in the treatment of a chemokine (such as CCR3) or H1 mediated disease state.

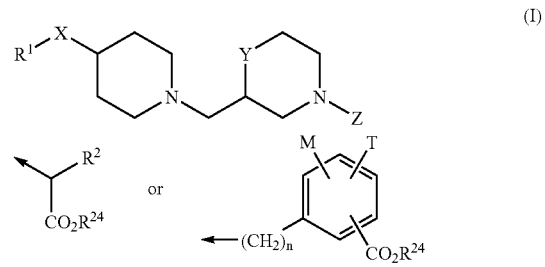

6 Claims, No Drawings

FOREIGN PATENT DOCUMENTS

| | | |
|---|---|---|
| WO | WO 00/00488 | 1/2000 |
| WO | WO 00/12478 | 3/2000 |
| WO | WO 00/32590 | 6/2000 |
| WO | WO 00/35877 A1 | 6/2000 |
| WO | WO 00/66559 | 11/2000 |
| WO | WO 01/02381 | 1/2001 |
| WO | WO 01/07436 | 2/2001 |
| WO | WO 01/29066 | 4/2001 |
| WO | WO 01/77101 | 10/2001 |
| WO | WO 01/92227 | 12/2001 |
| WO | WO 02/18335 | 3/2002 |
| WO | WO 02/20484 | 3/2002 |
| WO | WO 02/072570 | 9/2002 |
| WO | WO 02/079190 | 10/2002 |
| WO | WO 02/079194 | 10/2002 |
| WO | WO 02/081449 | 10/2002 |
| WO | WO 03/004487 | 1/2003 |
| WO | WO 03/018576 | 3/2003 |
| WO | WO 03/020716 | 3/2003 |
| WO | WO 03/024962 | 3/2003 |
| WO | WO 03/078421 | 9/2003 |
| WO | WO 2004/029041 | 4/2004 |
| WO | WO 2004/085423 | 10/2004 |
| WO | WO 2004/087659 | 10/2004 |
| WO | WO 2004/099144 | 11/2004 |
| WO | WO 2004/113323 | 12/2004 |
| WO | WO 2005/097775 | 10/2005 |
| WO | WO 2006/126947 | 11/2006 |
| WO | WO 2006/126948 | 11/2006 |
| WO | WO 2007/011293 | 1/2007 |

OTHER PUBLICATIONS

Allain et al., (2005) STN International, HCAPLUS Database, Columbus, OH, Accession No. 1992:187881, Reg. No. 46817-91-8, citing "Antidepressants and cognition: comparative effects of moclobemide, viloxazine and maprotiline", *Psychopharmacology* 106 (Suppl.).

Cohen et al., *Am. J. Clin. Pathol.* 105:589 (1996).

Hermans et al., "4-Substituted Piperidines. II. Reaction of 1-Benzyl-4-cyano-4-*t*-aminopiperidines with Organometallic Compounds", *J. Med. Chem.* 8(6):851-855 (1965) at p. 852 ("compound 12" in Table I).

Patani and La Voie, "Bioisosterism: A Rational Approach in Drug Design", *Chem. Rev.* 96:3147-3176 (1996).

STN International, File CAPLUS, CAPLUS accession No. 1988:630911, Document No. 109:230911, Lehmann, Jochen et al: "Lactones. XVIII. Synthesis of lactone-bridged 1,1-diarylpropanamines"; & *Arch. Pharm.* (Weinheim, Ger.) (1988), 321(8), 443-5.

Harada et al., "Novel *N*-[1-(1-Substituted 4-Piperidinylmethyl)-4-piperidinyl]benzamides as Potent Colonic Prokinetic Agents", *Bioorganic & Medicinal Chemistry Letters* 12:967-970 (2002).

Hodgson et al., "Chemokines and Drug Discovery", *Drug New Perspect* 17(5):335-338 (2004).

Hoffman et al., "The Preparation of 2-Hydrazinyl Esters in High Optical Purity from 2-Sulfonyloxy Esters", *Tetrahedron Letters* 31(21):2953-2956 (1990).

\* cited by examiner

PIPERIDINE DERIVATIVES USEFUL AS MODULATORS OF CHEMOKINE RECEPTOR ACTIVITY

CROSS-REFERENCE TO RELATED APPLICATIONS

This application is the national phase application under 35 U.S.C. § 371 of PCT International Application No. PCT/SE03/00443, filed Mar. 17, 2003, which claims priority to Swedish Application Serial No. 0200844-9, filed Mar. 19, 2002.

The present invention concerns piperidine derivatives having pharmaceutical activity, to processes for preparing such derivatives, to pharmaceutical compositions comprising such derivatives and to the use of such derivatives as active therapeutic agents.

Pharmaceutically active piperidine derivatives are disclosed in WO99/38514, WO99/04794 and WO00/35877.

Histamine is a basic amine, 2-(4-imidazolyl)-ethylamine, and is formed from histidine by histidine decarboxylase. It is found in most tissues of the body, but is present in high concentrations in the lung, skin and in the gastrointestinal tract. At the cellular level inflammatory cells such as mast cells and basophils store large amounts of histamine. It is recognized that the degranulation of mast cells and basophils and the subsequent release of histamine is a fundamental mechanism responsible for the clinical manifestation of an allergic process. Histamine produces its actions by an effect on specific histamine G-protein coupled receptors, which are of three main types, H1, H2 and H3. Histamine H1 antagonists comprise the largest class of medications used in the treatment of patients with allergic disorders, for example rhinitis and urticaria. H1 antagonists are useful in controlling the allergic response by for example blocking the action of histamine on post-capillary venule smooth muscle, resulting in decreased vascular permeability, exudation and oedema. The antagonists also produce blockade of the actions of histamine on the H1 receptors on c-type nociceptive nerve fibres, resulting in decreased itching and sneezing.

Chemokines are chemotactic cytokines that are released by a wide variety of cells to attract macrophages, T cells, eosinophils, basophils and neutrophils to sites of inflammation and also play a rôle in the maturation of cells of the immune system. Chemokines play an important rôle in immune and inflammatory responses in various diseases and disorders, including asthma and allergic diseases, as well as autoimmune pathologies such as rheumatoid arthritis and atherosclerosis. These small secreted molecules are a growing superfamily of 8-14 kDa proteins characterized by a conserved four cysteine motif. The chemokine superfamily can be divided into two main groups exhibiting characteristic structural motifs, the Cys-X-Cys (C—X—C, or α) and Cys-Cys (C—C, or β) families. These are distinguished on the basis of a single amino acid insertion between the NH-proximal pair of cysteine residues and sequence similarity.

The C—X—C chemokines include several potent chemoattractants and activators of neutrophils such as interleukin-8 (IL-8) and neutrophil-activating peptide 2(NAP-2).

The C—C chemokines include potent chemoattractants of monocytes and lymphocytes but not neutrophils such as human monocyte chemotactic proteins 1-3 (MCP-1, MCP-2 and MCP-3), RANTES (Regulated on Activation, Normal T Expressed and Secreted), eotaxin and the macrophage inflammatory proteins 1α and 1β (MIP-1α and MIP-1β).

Studies have demonstrated that the actions of the chemokines are mediated by subfamilies of G protein-coupled receptors, among which are the receptors designated CCR1, CCR2, CCR2A, CCP2B, CCR3, CCR4, CCR5, CCR6, CCR7, CCR8, CCR9, CCR10, CXCR1, CXCR2, CXCR3 and CXCR4. These receptors represent good targets for drug development since agents which modulate these receptors would be useful in the treatment of disorders and diseases such as those mentioned above.

Viral infections are known to cause lung inflammation. It has been shown experimentally that the common cold increases mucosal output of eotaxin in the airways. Instillation of eotaxin into the nose can mimic some of the signs and symptoms of a common cold. (See, Greiff L et al Allergy (1999) 54(11) 1204-8 [Experimental common cold increase mucosal output of eotaxin in atopic individuals] and Kawaguchi M et al Int. Arch. Allergy Immunol. (2000) 122 S1 44 [Expression of eotaxin by normal airway epithelial cells after virus A infection]).

The present invention provides a compound of formula (I):

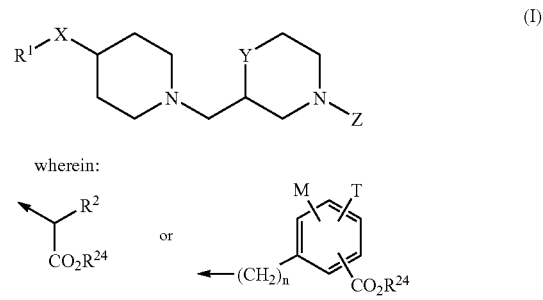

wherein:

Z is n is 0 or 1;
X is $CH_2$, C(O), O, S, S(O), $S(O)_2$ or $NR^3$;
Y is O or $CH_2$;
$R^1$ is hydrogen, $C_{1-6}$ alkyl, aryl or heterocyclyl;
$R_2$ is $C_{3-7}$ cycloalkyl {optionally substituted by $C_{1-4}$ alkyl, aryl or oxo}, $C_{3-7}$ cycloalkenyl {optionally substituted by oxo, $C_{1-6}$ alkyl or aryl}, aryl or heterocyclyl;

wherein the foregoing aryl and heterocyclyl moieties are optionally substituted by: halogen, cyano, nitro, hydroxy, oxo, $S(O)_p R^4$, $OC(O)NR^5 R^6$, $NR^7 R^8$, $NR^9 C(O)R^{10}$, $NR^{11}C(O)NR^{12}R^{13}$, $S(O)_2 NR^{14}R^{15}$, $NR^{16}S(O)_2 R^{17}$, $C(O)NR^{18}R^{19}$, $C(O)R^{20}$, $CO_2 R^{21}$, $NR^{22}CO_2 R^{23}$, $C_{1-6}$ alkyl, $C_{1-6}$ haloalkyl, $C_{1-6}$ alkoxy($C_{1-6}$)alkyl, $C_{1-6}$ alkoxy, $C_{1-6}$ haloalkoxy, $C_{1-6}$ alkoxy($C_{1-6}$)alkoxy, $C_{1-6}$ alkylthio, $C_{1-6}$ haloalkylthio, $C_{2-6}$ alkenyl, $C_{2-6}$ alkynyl, $C_{3-10}$ cycloalkyl (itself optionally substituted by $C_{1-4}$ alkyl or oxo), methylenedioxy, difluoromethylenedioxy, phenyl, phenyl($C_{1-4}$)alkyl, phenoxy, phenylthio, phenyl($C_{1-4}$)alkoxy, heterocyclyl, heterocyclyl($C_{1-4}$)alkyl, heterocyclyloxy or heterocyclyl($C_{1-4}$)alkoxy; wherein any of the immediately foregoing phenyl and heterocyclyl moieties are optionally substituted with halogen, hydroxy, nitro, $S(O)_q(C_{1-4}$ alkyl), $S(O)_2 NH_2$, cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$ (and these alkyl groups may join to form a ring as described for $R^5$ and $R^6$ below), $CO_2 H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$;

M and T are, independently, hydrogen, halogen, cyano, nitro, hydroxy, oxo, $S(O)_p R^4$, $OC(O)NR^5 R^6$, $NR^7 R^8$, $NR^9 C(O)R^{10}$, $NR^{11}C(O)NR^{12}R^{13}$, $S(O)_2 NR^{14}R^{15}$, $NR^{16}S(O)_2 R^{17}$, $C(O)NR^{18}R^{19}$, $C(O)R^{20}$, $CO_2 R^{21}$, $NR^{22}CO_2 R^{23}$, $C_{1-6}$ alkyl, $C_{1-6}$ haloalkyl, $C_{1-6}$ alkoxy($C_{1-6}$)alkyl, $C_{1-6}$ alkoxy, $C_{1-6}$ haloalkoxy, $C_{1-6}$ alkoxy($C_{1-6}$)alkoxy, $C_{1-6}$ alkylthio, $C_{1-6}$ haloalkylthio, $C_{2-6}$ alkenyl, $C_{2-6}$ alkynyl, $C_{3-10}$ cycloalkyl (itself optionally substituted by $C_{1-4}$ alkyl or oxo), methylenedioxy, difluoromethylenedioxy, phenyl, phenyl($C_{1-4}$)alkyl, phenoxy, phenylthio, phenyl($C_{1-4}$) alkoxy, heterocyclyl, heterocyclyl($C_{1-4}$)alkyl, heterocyclyloxy or heterocyclyl($C_{1-4}$)alkoxy; wherein any of the immediately foregoing phenyl and heterocyclyl moieties are optionally substituted with halogen, hydroxy, nitro, $S(O)_q(C_{1-4}$ alkyl), $S(O)_2NH_2$, cyano, $C_{1-4}$ allyl, $C_{1-4}$ alkoxy, $C(O)NH_2$, $C(O)NH(C_{1-4}$ alkyl), $C(O)N(C_{1-4}$ alkyl)$_2$ (and these alkyl groups may join to form a ring as described for $R^5$ and $R^6$ below), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$;

p and q are, independently, 0, 1 or 2;

$R^3, R^5, R^6, R^7, R^8, R^9, R^{10}, R^{11}, R^{12}, R^{13}, R^{14}, R^{15}, R^{16}, R^{18}, R^{19}, R^{20}, R^{21}$ and $R^{22}$ are, independently, hydrogen, $C_{1-6}$ alkyl (optionally substituted by halogen, hydroxy or $C_{3-10}$ cycloalkyl), $CH_2(C_{2-6}$ alkenyl), phenyl (itself optionally substituted by halogen, hydroxy, nitro, $NH_2$, $NH(C_{1-4}$ alkyl), $N(C_{1-4}$ alkyl)$_2$ (and these alkyl groups may join to form a ring as described for $R^5$ and $R^6$ below), $S(O)_2(C_{1-4}$ alkyl), $S(O)_2NH_2$, cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$ (and these alkyl groups may join to form a ring as described for $R^5$ and $R^6$ below), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$) or heterocyclyl (itself optionally substituted by halogen, hydroxy, nitro, $NH_2$, $NH(C_{1-4}$ alkyl), $N(C_{1-4}$ alkyl)$_2$ (and these alkyl groups may join to form a ring as described for $R^5$ and $R^6$ below), $S(O)_2(C_{1-4}$ alkyl), $S(O)_2NH_2$, $S(O)_2NH(C_{1-4}$ alkyl), $S(O)_2N(C_{1-4}$ alkyl)$_2$ (and these alkyl groups may join to form a ring as described for $R^5$ and $R^6$ below), cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$ (and these alkyl groups may join to form a ring as described for $R^5$ and $R^6$ below), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$);

alternatively $NR^5R^6$, $NR^7R^8$, $NR^{12}R^{13}$, $NR^{14}R^{15}$, $NR^{18}R^{19}$, may, independent, form a 4-7 membered heterocyclic ring, azetidine, pyrrolidine, piperidine, azepine, 1,4-morpholine or 1,4-piperazine, the latter optionally substituted by $C_{1-4}$ alkyl on the distal nitrogen;

$R^4$, $R^{17}$ and $R^{23}$ are, independently, $C_{1-6}$ alkyl (optionally substituted by halogen, hydroxy or $C_{3-10}$ cycloalkyl), $CH_2$ ($C_{2-6}$ alkenyl), phenyl (itself optionally substituted by halogen, hydroxy, nitro, $NH_2$, $NH(C_{1-4}$ alkyl), $N(C_{1-4}$ alkyl)$_2$ (and these alkyl groups may join to form a ring as described for $R^5$ and $R^6$ above), $S(O)_2(C_{1-4}$ alkyl), $S(O)_2NH_2$, $S(O)_2NH(C_{1-4}$ alkyl), $S(O)_2N(C_{1-4}$ alkyl)$_2$ (and these alkyl groups may join to form a ring as described for $R^5$ and $R^6$ above), cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$ (and these alkyl groups may join to form a ring as described for $R^5$ and $R^6$ above), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$) or heterocyclyl (itself optionally substituted by halogen, hydroxy, nitro, $NH_2$, $NH(C_{1-4}$ alkyl), $N(C_{1-4}$ alkyl)$_2$ (and these alkyl groups may join to form a ring as described for $R^5$ and $R^6$ above), $S(O)_2(C_{1-4}$ alkyl), $S(O)_2NH_2$, $S(O)_2NH(C_{1-4}$ alkyl), $S(O)_2N(C_{1-4}$ alkyl)$_2$ (and these alkyl groups may join to form a ring as described for $R^5$ and $R^6$ above), cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$ (and these alkyl groups may join to form a ring as described for $R^5$ and $R^6$ above), $CO_2H$, $CO_2(C_{1-4}$ alkyl), $NHC(O)(C_{1-4}$ alkyl), $NHS(O)_2$ ($C_{1-4}$ alkyl), $C(O)(C_{1-4}$ alkyl), $CF_3$ or $OCF_3$);

$R^{24}$ is hydrogen, $C_{1-6}$alkyl or benzyl;

or an N-oxide thereof; or a pharmaceutically acceptable salt thereof; or a solvate thereof.

Certain compounds of the present invention can exist in different isomeric forms (such as enantiomers, diastereomers, geometric isomers or tautomers). The present invention covers all such isomers and mixtures thereof in all proportions.

Suitable salts include acid addition salts such as a hydrochloride, dihydrochloride, hydrobromide, phosphate, acetate, diacetate, fumarate, maleate, tartrate, citrate, oxalate, methanesulphonate or p-toluenesulphonate. Another example of an addition salt is sulphate. Salts also include metal salts, such as a sodium, potassium, magnesium or calcium salt.

The compounds of the invention may exist as solvates (such as hydrates) and the present invention covers all such solvates.

Halogen includes fluorine, chlorine, bromine and iodine. Halogen is, for example, fluorine or chlorine.

Alkyl groups and moieties are straight or branched chain and are, for example, methyl, ethyl, n-propyl, iso-propyl or tert-butyl.

Alkenyl group are, for example, vinyl or allyl.

Cycloalkyl is mono-, bi or tricyclic and is, for example, cyclopropyl, cyclopentyl, cyclohexyl, norbornyl or camphoryl. The cycloalkyl ring is optionally fused to a benzene ring (for example forming a bicyclo[4.2.0]octa-1,3,5-trienyl or indanyl ring system).

Cycloalkenyl is, for example, monocyclic and is, for example, cyclopentenyl or cyclohexenyl.

Aryl is, for example, phenyl or naphthyl.

Heterocyclyl is an aromatic or non-aromatic 5 or 6 membered ring, optionally fused to one or more other rings, comprising at least one heteroatom selected from the group comprising nitrogen, oxygen and sulphur; or an N-oxide thereof, or an S-oxide or S-dioxide thereof. Heterocyclyl is, for example, furyl, thienyl (also known as thiophenyl), pyrrolyl, 2,5-dihydropyrrolyl, thiazolyl, pyrazolyl, oxazolyl, isoxazolyl, imidazolyl, piperidinyl, morpholinyl, pyridinyl (for example in 6-oxo-1,6-dihydro-pyridinyl), pyrimidinyl, indolyl, 2,3-dihydroindolyl, benzo[b]furyl (also known as benzfuryl), benz[b]thienyl (also known as benzthienyl or benzthiophenyl), 2,3-dihydrobenz[b]thienyl (for example in 1-dioxo-2,3-dihydrobenz[b]tienyl), indazolyl, benzimidazolyl, benztriazolyl, benzoxazolyl, benzthiazolyl (for example in 1H-benzthiazol-2-one-yl), 2,3-dihydrobenzthiazolyl (for example in 2,3-dihydrobenzthiazol-2-one-yl), 1,2,3-benzothiadiazolyl, an imidazopyridinyl (such as imidazo[1,2a]pyridinyl), thieno[3,2-b]pyridin-6-yl 1,2,3-benzoxadiazolyl, benzo[1,2,3]thiadiazolyl, 2,1,3-benzothiadiazolyl, benzofurazan (also known as 2,1,3-benzoxadiazolyl), quinoxalinyl, dihydro-1-benzopyryliumyl (for example in a coumarinyl or a chromonyl), 3,4-dihydro-1H-2,1-benzothiazinyl (for example in 2-dioxo-3,4-dihydro-1H-2,1-benzothiazinyl), a pyrazolopyridine (for example 1H-pyrazolo[3,4b]pyridinyl), a purine (for example in 3,7-dihydro-purin-2,6-dione-8-yl), quinolinyl, isoquinolinyl (for example in 2H-isoquinolin-1-one-yl), a naphthyridinyl (for example [1,6]naphthyridinyl or [1,8]naphthyridinyl or in 1H-[1,8]naphthyridin-4-one-yl), a benzothiazinyl (for example in 4H-benzo[1,4]thiazin-3-one-yl), benzo[d]imidazo[2,1-b] thiazol-2-yl or dibenzothiophenyl (also known as dibenzothienyl); or an N-oxide thereof, or an S-oxide or S-dioxide thereof. Heterocyclyl also includes isothiazolyl.

In one aspect the present invention provides a compound of formula (Ia):

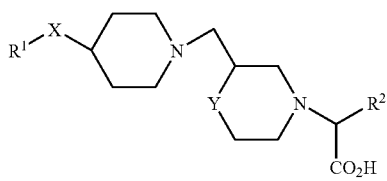

(Ia)

wherein: X is $CH_2$, $C(O)$, O, S, $S(O)$, $S(O)_2$ or $NR^3$; Y is O or $CH_2$; $R^1$ is hydrogen, $C_{1-6}$ alkyl, aryl or heterocyclyl; $R^2$ is $C_{3-7}$ cycloalkyl {optionally substituted by $C_{1-4}$ alkyl, aryl or oxo}, $C_{3-7}$ cycloalkenyl {optionally substituted by oxo, $C_{1-6}$ alkyl or aryl}, aryl or heterocyclyl; wherein the foregoing aryl and heterocyclyl moieties are optionally substituted by: halogen, cyano, nitro, hydroxy, oxo, $S(O)_pR^4$, $OC(O)NR^5R^6$, $NR^7R^8$, $NR^9C(O)R^{10}$, $NR^{11}C(O)NR^{12}R^{13}$, $S(O)_2NR^{14}R^{15}$, $NR^{16}S(O)_2R^{17}$, $C(O)NR^{18}R^{19}$, $C(O)R^{20}$, $CO_2R^{21}$, $NR^{22}CO_2R^{23}$, $C_{1-6}$ alkyl, $C_{1-6}$ haloalkyl, $C_{1-6}$ alkoxy($C_{1-6}$) alkyl, $C_{1-6}$ alkoxy, $C_{1-6}$ haloalkoxy, $C_{1-6}$ alkoxy($C_{1-6}$)alkoxy, $C_{1-6}$ alkylthio, $C_{1-6}$ haloalkylthio, $C_{2-6}$ alkenyl, $C_{2-6}$ alkynyl, $C_{3-10}$ cycloalkyl (itself optionally substituted by $C_{1-4}$ alkyl or oxo), methylenedioxy, difluoromethylenedioxy, phenyl, phenyl($C_{1-4}$)alkyl, phenoxy, phenylthio, phenyl($C_{1-4}$)alkoxy, heteroaryl, heteroaryl($C_{1-4}$)alkyl, heteroaryloxy or heteroaryl ($C_{1-4}$)alkoxy; wherein any of the immediately foregoing phenyl and heteroaryl moieties are optionally substituted with halogen, hydroxy, nitro, $S(O)_q(C_{1-4}$ alkyl), $S(O)_2NH_2$, cyano, $C_{1-4}$ alkyl, $C_{1-4}$ alkoxy, $C(O)NH_2$, $C(O)NH(C_{1-4}$ alkyl), $C(O)N(C_{1-4}$ alkyl$)_2$ (and these alkyl groups may join to form a ring as described for $R^5$ and $R^6$ below), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$; p and q are, independently, 0, 1 or 2; $R^3$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{18}$, $R^{19}$, $R^{20}$, $R^{21}$ and $R^{22}$ are, independently, hydrogen, $C_{1-6}$ alkyl (optionally substituted by halogen, hydroxy or $C_{3-10}$ cycloalkyl), $CH_2(C_{2-6}$ alkenyl), phenyl (itself optionally substituted by halogen, hydroxy, nitro, $NH_2$, $NH(C_{1-4}$ alkyl), $N(C_{1-4}$ alkyl$)_2$, $S(O)_2(C_{1-4}$ alkyl), $S(O)_2NH_2$, cyano, $C_{1-4}$ alkyl, $C_{1-4}$ alkoxy, $C(O)NH_2$, $C(O)NH(C_{1-4}$ alkyl), $C(O)N(C_{1-4}$ alkyl$)_2$ (and these alkyl groups may join to form a ring as described for $R^5$ and $R^6$ below), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$) or heterocyclyl (itself optionally substituted by halogen, hydroxy, nitro, $NH_2$, $NH(C_{1-4}$ alkyl), $N(C_{1-4}$ alkyl$)_2$ (and these alkyl groups may join to form a ring as described for $R^5$ and $R^6$ below), $S(O)_2(C_{1-4}$ alkyl), $S(O)_2NH_2$, $S(O)_2NH(C_{1-4}$ alkyl), $S(O)_2N(C_{1-4}$ alkyl$)_2$ (and these alkyl groups may join to form a ring as described for $R^5$ and $R^6$ below), cyano, $C_{1-4}$ alkyl, $C_{1-4}$ alkoxy, $C(O)NH_2$, $C(O)NH(C_{1-4}$ alkyl), $C(O)N(C_{1-4}$ alkyl$)_2$ (and these alkyl groups may join to form a ring as described for $R^5$ and $R^6$ below), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$); alternatively $NR^5R^6$, $NR^7R^8$, $NR^{12}R^{13}$, $NR^{14}R^{15}$, $NR^{18}R^{19}$, may, independently, form a 4-7 membered heterocyclic ring, azetidine, pyrrolidine, piperidine, azepine, 1,4-morpholine or 1,4-piperazine, the latter optionally substituted by $C_{1-4}$ alkyl on the distal nitrogen; $R^4$, $R^{17}$ and $R^{23}$ are, independently, $C_{1-6}$ alkyl (optionally substituted by halogen, hydroxy or $C_{3-10}$ cycloalkyl), $CH_2(C_{2-6}$ alkenyl), phenyl (itself optionally substituted by halogen, hydroxy, nitro, $NH_2$, $NH(C_{1-4}$ alkyl), $N(C_{1-4}$ alkyl$)_2$ (and these alkyl groups may join to form a ring as described for $R^5$ and $R^6$ above), $S(O)_2(C_{1-4}$ alkyl), $S(O)_2NH_2$, $S(O)_2NH(C_{1-4}$ alkyl), $S(O)_2N(C_{1-4}$ alkyl$)_2$ (and these alkyl groups may join to form a ring as described for $R^5$ and $R^6$ above), cyano, $C_{1-4}$ alkyl, $C_{1-4}$ alkoxy, $C(O)NH_2$, $C(O)NH(C_{1-4}$ alkyl), $C(O)N(C_{1-4}$ alkyl$)_2$ (and these alkyl groups may join to form a ring as described for $R^5$ and $R^6$ above), $CO_2H$, $CO_2(C_{1-4}$ alkyl), $NHC(O)(C_{1-4}$ alkyl), $NHS(O)_2(C_{1-4}$ alkyl $C(O)(C_{1-4}$ alkyl), $CF_3$ or $OCF_3$) or heterocyclyl (itself optionally substituted by halogen, hydroxy, nitro, $NH_2$, $NH(C_{1-4}$ alkyl), $N(C_{1-4}$ alkyl$)_2$ (and these alkyl groups may join to form a ring as described for $R^5$ and $R^6$ above), $S(O)_2(C_{1-4}$ alkyl), $S(O)_2NH_2$, $S(O)_2NH(C_{1-4}$ alkyl), $S(O)_2N(C_{1-4}$ alkyl$)_2$ (and these alkyl groups may join to form a ring as described for $R^5$ and $R^6$ above), cyano, $C_{1-4}$ alkyl, $C_{1-4}$ alkoxy, $C(O)NH_2$, $C(O)NH(C_{1-4}$ alkyl), $C(O)N(C_{1-4}$ alkyl$)_2$ (and these alkyl groups may join to form a ring as described for $R^5$ and $R^6$ above), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$); or an N-oxide thereof; or a pharmaceutically acceptable salt thereof;

or a solvate thereof.

In one particular aspect the invention provides a compound of the invention wherein X is O.

In a further aspect the invention provides a compound of the invention wherein Y is O.

In a still further aspect the invention provides a compound of the invention wherein Y is $CH_2$.

In another aspect $R^{24}$ is hydrogen.

In yet another aspect Z is $CHR^2CO_2R^{24}$.

In another aspect $R^1$ is phenyl optionally substituted with fluorine, chlorine, $C_{1-4}$ alkyl (for example methyl) or $C_{1-4}$ alkoxy (for example methoxy). In another aspect $R^1$ is phenyl optionally substituted with fluorine, chlorine or $C_{1-4}$ alkyl (for example methyl).

In a further aspect $R^1$ is phenyl optionally substituted (for example with one, two or three) with fluorine, chlorine, $C_{1-4}$ alkyl (for example methyl) or $C_{1-4}$ alkoxy (for example methoxy). In a still further aspect $R^1$ is phenyl substituted by one, two or three of fluorine, chlorine, methyl or methoxy. For example $R^1$ is 3,4-dichlorophenyl, 2,4-dichloro-3-methylphenyl, 3,4-dichloro-2-methylphenyl, 2,4-dichlorophenyl, 4-chloro-2-methylphenyl or 2-chloro-4-fluorophenyl.

In a further aspect $R^2$ is unsubstituted phenyl, mono-, di- or tri-substituted phenyl, unsubstituted or mono-substituted naphthyl or mono-substituted heterocyclyl, the substituents being chosen from those described above.

In a still further aspect $R^2$ is oxo substituted heterocyclyl, said heterocyclyl optionally further substituted with one or more substituents chosen from those described above.

In another aspect $R^2$ is phenyl or heterocyclyl, either of which is optionally substituted by: halo, hydroxy, nitro, cyano, amino, $C_{1-4}$ alkyl (itself optionally substituted by $S(O)_2(C_{1-4}$ alkyl) or $S(O)_2$phenyl), $C_{1-4}$ alkoxy, $S(O)_pR^4$ (wherein p is 0, 1 or 2 (such as 2)), $C(O)NH_2$, $NHS(O)_2(C_{1-4}$ alkyl), $S(O)_2NH_2$, $S(O)_2NH(C_{1-4}$ alkyl) or $S(O)_2N(C_{1-4}$ alkyl$)_2$; and $R^4$ is $C_{1-4}$ allyl, $C_{1-4}$ hydroxyalkyl, $C_{3-7}$ cycloalkyl or $C_{3-7}$ cycloalkyl($C_{1-4}$ alkyl) (such as cyclopropylmethyl).

In a further aspect $R^2$ is phenyl optionally mono-substituted by: halo, hydroxy, nitro, cyano, amino, $C_{1-4}$ alkyl (itself optionally substituted by $S(O)_2(C_{1-4}$ alkyl) or $S(O)_2$phenyl), $C_{1-4}$ alkoxy, $S(O)_pR^4$ (wherein p is 0, 1 or 2 (such as 2)), $C(O)NH_2$, $NHS(O)_2(C_{1-4}$ alkyl), $S(O)_2NH_2$, $S(O)_2NH(C_{1-4}$ alkyl) or $S(O)_2N(C_{1-4}$ alkyl$)_2$; and $R^4$ is $C_{1-4}$ alkyl, $C_{1-4}$ hydroxyalkyl, $C_{3-7}$ cycloalkyl or $C_{3-7}$ cycloalkyl($C_{1-4}$ alkyl) (such as cyclopropylmethyl).

Heterocyclyl includes thienyl, furanyl or benzofuranyl; for example furanyl monosubstituted by $C_{1-4}$ alkyl.

In yet another aspect $R^2$ is phenyl (optionally substituted by halogen, hydroxy, $C_{1-6}$ alkyl, $C_{1-6}$ alkoxy, benzyloxy or 9H-carbazylmethyl), naphthylenyl (optionally substituted by $C_{1-4}$ alkoxy) or heterocyclyl (optionally substituted by $C_{1-4}$ alkyl).

In a further aspect the present invention provides a compound of formula (I) wherein X is O; Y is O or $CH_2$; $R^1$ is phenyl optionally substituted by halogen (for example chlorine) or $C_{1-4}$ alkyl (for example methyl); and $R^2$ is as defined above.

A compound of the invention, wherein Z is $CHR^2CO_2R^{24}$, can be prepared by coupling a compound of formula (II):

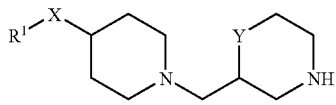
(II)

with a compound of formula (III):

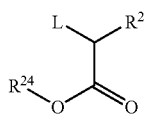
(III)

wherein L is a suitable leaving group (for example halogen or $C_{1-6}$ alkylsulfonyl) and the coupling can be carried out in a suitable solvent (such as water).

Alternatively, a compound of the invention, wherein Z is $CHR^2CO_2R^{24}$, can be prepared by reductive amination of a compound (II) with an ester (such as a $C_{1-6}$ alkyl ester or a benzyl ester) compound of formula (IIIa):

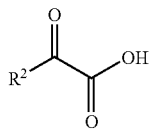
(IIIa)

in the presence of $NaBH(OAc)_3$ and acetic acid, followed optionally by removal of the ester group.

Alternatively, a compound of the invention, wherein Z is $CHR^2CO_2R^{24}$, can be prepared by a three component coupling of a compound of formula (II) with compounds of formula (IIIb) and (IIIc):

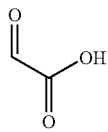
(IIIb)

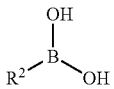
(IIIc)

A compound of formula (II), where X is $CH_2$, may be prepared following methods in WO 00/35877. A compound of formula (II) can be prepared by deprotecting a compound of formula (IV):

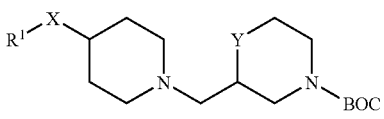
(IV)

for example using trifluoroacetic acid in a suitable solvent (such as dichloromethane) or using a source of hydrogen chloride in a suitable solvent (such as dioxane).

A compound of formula (IV), wherein X is O, can be prepared by reacting a compound of formula (V):

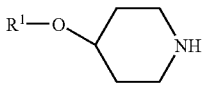
(V)

with a compound of formula (VI):

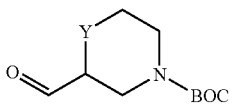
(VI)

in the presence of $NaBH(OAc)_3$ and acetic acid.

Alternatively, a compound of formula (IV), wherein X is O, can be prepared by reacting a compound of formula (V) with a compound of formula (VIa):

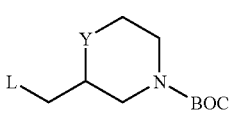
(VIa)

where L represents a suitable leaving group, for example mesylate, in the presence of a suitable base, for example, potassium carbonate, in a suitable solvent, such as acetone.

A compound of formula (IV), wherein X is CO or CH$_2$, can be prepared by oxidizing or reducing a compound of formula (VII):

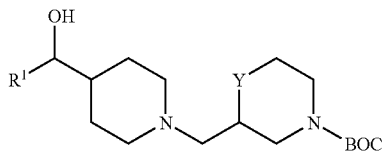
(VII)

A compound of formula (VII) can be prepared by reacting a compound of formula (VIII):

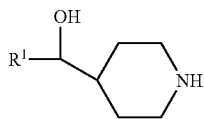
(VIII)

with a compound of formula (VI) in the presence of NaBH(OAc)$_3$ and acetic acid. A compound of formula (VIII) can be prepared by reduction of a compound of formula (IX):

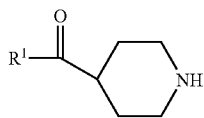
(IX)

A compound of formula (IV) wherein X is NR$^3$ can be prepared by reacting a compound of formula (X):

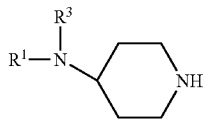
(X)

with a compound of formula (VI) in the presence of NaBH(OAc)$_3$ and acetic acid. A compound of formula (X) can be prepared by reacting NHR$^1$R$^3$ with a compound of formula (XI):

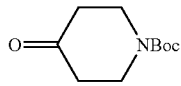
(XI)

in the presence of NaBH(OAc)$_3$ and acetic acid and then deprotecting the piperidine nitrogen {for example using trifluoroacetic acid in a suitable solvent (such as dichloromethane) or using a source of hydrogen chloride in a suitable solvent (such as dioxane)}.

A compound of formula (I) wherein:

Z is 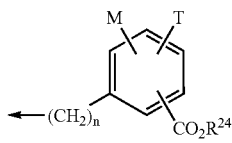

can be prepared by reacting a compound of formula (II) with:
when n is 1, a compound of formula (XIV):

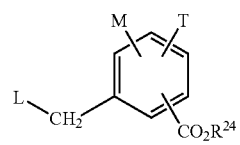
(XIV)

wherein L is a leaving group (such as chlorine, bromine or OS(O)$_2$CH$_3$);
when n is 1, a compound of formula (XVI):

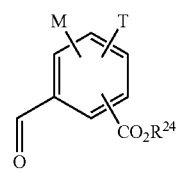
(XVI)

under reductive amination conditions (for example using NaBH(OAc)$_3$ and acetic acid in tetrahydrofuran); and, when n is 0, a compound of formula (XV):

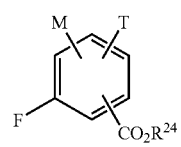
(XV)

in the presence of potassium carbonate, in a suitable solvent (such as N,N-dimethylformamide) at a suitable temperature (such as in the range 80-110° C.).

Compounds of the invention where R$^{24}$ is hydrogen may be converted to compounds of the invention where R$^{24}$ is not hydrogen by standard esterifcation methods well known in the art.

Compounds of the invention where R$^{24}$ is not hydrogen may be converted to compounds of the invention where R$^{24}$ is hydrogen by standard ester hydrolysis methods well known in the art.

A compound of formula (VI) or formula (VIa) may be prepared by following methods described in WO 00/35877. Alternatively a compound of formula (VI) or (VIa) can be prepared by routes described in the literature from the corresponding alcohol (for example: when Y is CH$_2$ see Tet. Asym., 1992, 3, 1049; Bioorg. Med. Chem. Lett., 1997, 7, 1525 and 1998, 8, 1595; and when Y is O see Farmaco. Ed. Sci., 1994, 49, 77; Heterocycles, 1994, 38, 1033 and 1993, 35, 105).

Further compounds of the invention can be prepared by adaptation of the routes described above, methods described in the art, or the Examples recited below.

Compounds of formula (V), (VI), (IX) and (XI) can be prepared by using or adapting methods described in the art.

In another aspect the present invention provides processes for the preparation of compounds of the invention.

The compounds of the invention have activity as pharmaceuticals, in particular as modulators of chemokine receptor (for example CCR3) activity, and may be used in the treatment of autoimmune, inflammatory, proliferative or hyperproliferative diseases, or immunologically-mediated diseases (including rejection of transplanted organs or tissues and Acquired Immunodeficiency Syndrome (AIDS)).

Examples of these conditions are:
(1) (the respiratory tract) obstructive diseases of airways including: chronic obstructive pulmonary disease (COPD) (such as irreversible COPD); asthma {such as bronchial, allergic, intrinsic, extrinsic or dust asthma, particularly chronic or inveterate asthma (for example late asthma or airways hyper-responsiveness)}; bronchitis {such as eosinophilic bronchitis}; acute, allergic, atrophic rhinitis or chronic rhinitis including rhinitis caseosa, hypertrophic rhinitis, rhinitis purulenta, rhinitis sicca or rhinitis medicamentosa; membranous rhinitis including croupous, fibrinous or pseudomembranous rhinitis or scrofulous rhinitis; seasonal rhinitis including rhinitis nervosa (hay fever) or vasomotor rhinitis; sarcoidosis; farmer's lung and related diseases; nasal polyposis; fibroid lung, idiopathic interstitial pneumonia, antitussive activity, treatment of chronic cough associated with inflammatory conditions of the airways or iatrogenic induced cough;
(2) (bone and joints) arthrides including rheumatic, infectious, autoimmune, seronegative spondyloarthropathies (such as ankylosing spondylitis, psoriatic arthritis or Reiter's disease), Behcet's disease, Sjogren's syndrome or systemic sclerosis;
(3) (skin and eyes) psoriasis, atopic dermatitis, contact dermatitis or other eczmatous dermitides, seborrhoetic dermatitis, lichen planus, phemphigus, bullous phemphigus, epidermolysis bullosa, urticaria, angiodermas, vasculitides erythemas, cutaneous eosinophilias, uveitis, alopecia areata, corneal ulcer or vernal conjunctivitis;
(4) (gastrointestinal tract) Coeliac disease, proctitis, eosinophilic gastro-enteritis, mastocytosis, Crohn's disease, ulcerative colitis, irritable bowel disease or food-related allergies which have effects remote from the gut (for example migraine, rhinitis or eczema);
(5) (Allograft rejection) acute and chronic following, for example, transplantation of kidney, heart, liver, lung, bone marrow, skin or cornea; or chronic graft versus host disease; and/or
(6) (other tissues or diseases) Alzheimer's disease, multiple sclerosis, atherosclerosis, Acquired Immunodeficiency Syndrome (AIDS), lupus disorders (such as lupus erythematosus or systemic lupus), erythematosus, Hashimoto's thyroiditis, myasthenia gravis, type I diabetes, nephrotic syndrome, eosinophilia fascitis, hyper IgE syndrome, leprosy (such as lepromatous leprosy), peridontal disease, Sezary syndrome, idiopathic thrombocytopenia pupura or disorders of the menstrual cycle.

The compounds of the invention or a pharmaceutically acceptable salt thereof or a solvate thereof, are also H1 antagonists (and can, therefore, be used in the treatment of allergic disorders); and may also be used to control a sign and/or symptom of what is commonly referred to as a cold (for example a sign and/or symptom of a common cold or influenza or other associated respiratory virus infection).

According to a further feature of the present invention there is provided a method for treating a chemokine mediated disease state (for example a CCR3 mediated disease state) in a mammal, such as man, suffering from, or at risk of, said disease state, which comprises administering to a mammal in need of such treatment a therapeutically effective amount of a compound of the formula (I) or (Ia) or a pharmaceutically acceptable salt thereof or a solvate thereof.

According to another feature of the present invention there is provided a method for antagonizing H1 in a mammal, such as man, suffering from, or at risk of, an H1 mediated disease state, which comprises administering to a mammal in need of such treatment a therapeutically effective amount of a compound of the formula (I) or (Ia) or a pharmaceutically acceptable salt thereof or a solvate thereof.

According to yet another feature of the present invention there is provided a method for treating a sign and/or symptom of what is commonly referred to as a cold in a mammal, such as man, suffering from, or at risk of, said disease state, which comprises administering to a mammal in need of such treatment a therapeutically effective amount of a compound of the formula (I) or (Ia) or a pharmaceutically acceptable salt thereof or a solvate thereof.

The invention also provides a compound of the formula (I) or (Ia), or a pharmaceutically acceptable salt thereof or a solvate thereof, for use in therapy.

In another aspect the invention provides the use of a compound of formula (I) or (Ia), or a pharmaceutically acceptable salt thereof or a solvate thereof, in the manufacture of a medicament for use in therapy (for example modulating chemokine receptor activity (for example CCR3 receptor activity), antagonizing H1 or treating a sign and/or symptom of what is commonly referred to as a cold).

The invention further provides the use of a compound of formula (I) or (Ia), or a pharmaceutically acceptable salt thereof, in the manufacture of a medicament for use in the treatment of:
(1) (the respiratory tract) obstructive diseases of airways including: chronic obstructive pulmonary disease (COPD) (such as irreversible COPD); asthma {such as bronchial, allergic, intrinsic, extrinsic or dust asthma, particularly chronic or inveterate asthma (for example late asthma or airways hyper-responsiveness)}; bronchitis {such as eosinophilic bronchitis}; acute, allergic, atrophic rhinitis or chronic rhinitis including rhinitis caseosa, hypertrophic rhinitis, rhinitis purulenta, rhinitis sicca or rhinitis medicamentosa; membranous rhinitis including croupous, fibrinous or pseudomembranous rhinitis or scrofulous rhinitis; seasonal rhinitis including rhinitis nervosa (hay fever) or vasomotor rhinitis; sarcoidosis; farmer's lung and related diseases; nasal polyposis; fibroid lung, idiopathic interstitial pneumonia, antitussive activity, treatment of chronic cough associated with inflammatory conditions of the airways or iatrogenic induced cough;
(2) (bone and joints) arthrides including rheumatic, infectious, autoimmune, seronegative spondyloarthropathies (such as ankylosing spondylitis, psoriatic arthritis or Reiter's disease), Behcet's disease, Sjogren's syndrome or systemic sclerosis;
(3) (skin and eyes) psoriasis, atopic dermatitis, contact dermatitis or other eczmatous dermitides, seborrhoetic dermatitis, lichen planus, phemphigus, bullous phemphigus, epidermolysis bullosa, urticaria, angiodermas, vasculitides erythemas, cutaneous eosinophilias, uveitis, alopecia areata, corneal ulcer or vernal conjunctivitis;

(4) (gastrointestinal tract) Coeliac disease, proctitis, eosinophilic gastro-enteritis, mastocytosis, Crohn's disease, ulcerative colitis, irritable bowel disease or food-related allergies which have effects remote from the gut (for example migraine, rhinitis or eczema);

(5) (Allograft rejection) acute and chronic following, for example, transplantation of kidney, heart, liver, lung, bone marrow, skin or cornea; or chronic graft versus host disease; and/or (6) (other tissues or diseases) Alzheimer's disease, multiple sclerosis, atherosclerosis, Acquired Immunodeficiency Syndrome (AIDS), lupus disorders (such as lupus erythematosus or systemic lupus), erythematosus, Hashimoto's thyroiditis, myasthenia gravis, type I diabetes, nephrotic syndrome, eosinophilia fascitis, hyper IgE syndrome, leprosy (such as lepromatous leprosy), Peridontal disease, sezary syndrome, idiopathic thrombocytopenia pupura or disorders of the menstrual cycle;

in a mammal (for example man).

In a further aspect the invention provides a compound of formula (I) or (Ia), or a pharmaceutically acceptable salt thereof, for use in the treatment of asthma {such as bronchial, allergic, intrinsic, extrinsic or dust asthma, particularly chronic or inveterate asthma (for example late asthma or airways hyper-responsiveness)}; or rhinitis {including acute, allergic, atrophic or chronic rhinitis, such as rhinitis caseosa, hypertrophic rhinitis, rhinitis purulenta, rhinitis sicca or rhinitis medicamentosa; membranous rhinitis including croupous, fibrinous or pseudomembranous rhinitis or scrofulous rhinitis; seasonal rhinitis including rhinitis nervosa (ay fever) or vasomotor rhinitis}.

In a still further aspect a compound of formula (I) or (Ia), or a pharmaceutically acceptable salt thereof, is useful in the treatment of asthma.

The present invention also provides a the use of a compound of formula (I) or (Ia), or a pharmaceutically acceptable salt thereof, in the manufacture of a medicament for use in the treatment of asthma {such as bronchial, allergic, intrinsic, extrinsic or dust asthma, particularly chronic or inveterate asthma (for example late asthma or airways hyper-responsiveness)}; or rhinitis {including acute, allergic, atrophic or chronic rhinitis, such as rhinitis caseosa, hypertrophic rhinitis, rhinitis purulenta, rhinitis sicca or rhinitis medicamentosa; membranous rhinitis including croupous, fibrinous or pseudomembranous rhinitis or scrofalous rhinitis; seasonal rhinitis including rhinitis nervosa (hay fever) or vasomotor rhinitis}.

In order to use a compound of the invention, or a pharmaceutically acceptable salt thereof or solvate thereof, for the therapeutic treatment of a mammal, such as man, said ingredient is normally formulated in accordance with standard pharmaceutical practice as a pharmaceutical composition. Therefore in another aspect the present invention provides a pharmaceutical composition which comprises a compound of the formula (I) or (Ia), or a pharmaceutically acceptable salt thereof or a solvate thereof (active ingredient), and a pharmaceutically acceptable adjuvant, diluent or carrier.

In a further aspect the present invention provides a process for the preparation of said composition which comprises mixing active ingredient with a pharmaceutically acceptable adjuvant, diluent or carrier. Depending on the mode of administration, the pharmaceutical composition will, for example, comprise from 0.05 to 99% w (per cent by weight), such as from 0.05 to 80% w, for example from 0.10 to 70% w, and such as from 0.10 to 50% w, of active ingredient, all percentages by weight being based on total composition.

The pharmaceutical compositions of this invention may be administered in standard manner for the disease condition that it is desired to treat, for example by topical (such as to the lung and/or airways or to the skin), oral, rectal or parenteral administration. For these purposes the compounds of this invention may be formulated by means known in the art. A suitable pharmaceutical composition of this invention is one suitable for oral administration in unit dosage form, for example a tablet or capsule which contains between 0.1 mg and 1 g of active ingredient.

Each patient may receive, for example, a dose of 0.01 $mgkg^{-1}$ to 100 $mgkg^{-1}$, such as in the range of 0.1 $mgkg^{-1}$ to 20 $mgkg^{-1}$, of the active ingredient administered, for example, 1 to 4 times per day.

The invention will now be illustrated by the following non-limiting examples in which, unless stated otherwise:

(i) when given, $^1H$ NMR data is quoted and is in the form of delta values for major diagnostic protons, given in parts per million (ppm) relative to tetramethylsilane (TMS) as an internal standard, determined at 300 MHz or 400 MHz using perdeuterio DMSO-D6 ($CD_3SOCD_3$) or $CDCl_3$ as the solvent unless otherwise stated;

(ii) mass spectra (MS) were run with an electron energy of 70 electron volts in the chemical ionization (CI) mode using a direct exposure probe; where indicated ionization was effected by electron impact (EI) or fast atom bombardment (FAB); where values for m/z are given, generally only ions which indicate the parent mass are reported, and unless otherwise stated the mass ion quoted is the positive mass ion—$(M+H)^+$;

(iii) the title and sub-title compounds of the examples and methods were named using the Index name program from Advanced Chemistry Development Inc.;

(iv) unless stated otherwise, reverse phase HPLC was conducted using a Symmetry™, NovaPak™ or Xerra™ reverse phase silica column; and (v) the following abbreviations are used:

| RT | room temperature |
|---|---|
| Boc or BOC | tert-butoxycarbonyl |
| HPLC | high pressure liquid chromatography |
| DMSO | dimethylsulfoxide |
| aq | aqueous |

Preparation 1

(2S) 2-[[4-(3,4-Dichlorophenoxy)-1-piperidinyl] methyl]-morpholine (Intermediate 1)

Step a: (2S) 1,1-Dimethylethyl 2-[[(methylsulfonyl) oxy]methyl]-2-(hydroxymethyl)-4-morpholinecarboxylate To a solution of (2S) 1,1-dimethylethyl 2-(hydroxymethyl)-4-morpholinecarboxylate (5.63 g) (Heterocycles, 1993, 35, 105) and N-ethyl-N,N-diisopropylamine (9 ml) in dichloromethane (200 ml) at room temperature was added methanesulfonic anhydride (5.42 g). The reaction was stirred for 16 hours. The reaction mixture was poured onto saturated aqueous $NaHCO_3$ solution and the organics were extracted with dichloromethane. The combined organic extracts were dried with $MgSO_4$ and concentrated to give an oil (8.33 g). This was used without further purification.

Step b: (2R) 1,1-Dimethylethyl 2-[[4-(3,4-dichlorophenoxy)-1-piperidinyl]methyl]-4-morpholinecarboxylate To a solution of 4-(3,4-dichlorophenoxy)piperidine (WO 01/77101; 9.22 g) dissolved in acetonitrile (60 ml) was added the product of Step (a) (5.53 g). The mixture was refluxed for 12 hrs and the solvents were evaporated. Purification by flash chromatography eluting with dichloromethane:methanol:NH$_3$ (aq) (2:97.9:0.1) gave the sub-title compound as an oil (5.76 g).

$^1$H NMR (CDCl$_3$) δ 1.47 (9H, s), 1.87-1.77 (2H, m), 2.02-1.94 (2H, m), 2.39-2.30 (2H, m), 2.60-2.51 (2H, m), 2.77-2.70 (2H, m), 2.95-2.89 (1H, m), 3.58-3.50 (2H, m), 3.73-3.67 (1H, m), 3.96-3.81 (2H, m), 4.30-4.22 (2H, m), 6.75 (1H, dd), 6.99 (1H, d), 7.30 (1H, d)

Step c: (2S) 2-[[4-(3,4-Dichlorophenoxy)-1-piperidinyl]methyl]morpholine

The product from Step (b) (5.76 g) was dissolved in dichloromethane (100 ml) and trifluoroacetic acid (40 ml) was added. After 16 hours at room temperature the solution was evaporated. The free base was liberated by addition of aqueous NaOH (2M) and extraction with dichloromethane. The combined organic extracts were dried with MgSO$_4$ and concentrated. Purification by flash chromatography eluting with dichloromethane:methanol:NH$_3$ (aq) (8:91.9:0.1) gave the title compound as an oil (3.84 g).

$^1$H NMR (CDCl$_3$) δ 1.75-1.88 (2H, m), 1.92-2.04 (2H, m), 2.23-2.39 (3H, m), 2.47-2.58 (2H, m), 2.72-2.93 (5H, m), 3.55-3.65 (2H, m), 3.86-3.90 (1H, m), 4.22-4.31 (1H, m), 6.75 (1H, dd), 6.99 (1H, d), 7.30 (1H, d)

Preparation 2

(2R) 2-[[4-(3,4-Dichlorophenoxy)-1-piperidinyl]methyl]-morpholine (Intermediate 2)

Prepared analogously to the S isomer in Preparation 1 starting with the antipodal morpholine in Step a of Preparation 1.

Preparation 3

(2S) 2-[[4-(2,4-Dichloro-3-methylphenoxy)-1-piperidinyl]methyl]-morpholine (Intermediate 3)

Prepared analogously to Preparation 1 starting with the appropriate phenoxypiperidine (WO 01/77101) in Step a of Preparation 1.

$^1$H NMR (CDCl$_3$) δ 1.83-2.04 (4H, m), 2.25-2.60 (8H, m), 2.69-2.95 (5H, m), 3.55-3.70 (2H, m), 3.86 (1H, d), 4.35 (1H, s), 6.74 (1H, d), 7.18 (1H, d)

Preparation 4

(2R) 2-[[4-(2,4-Dichloro-3-methylphenoxy)-1-piperidinyl]methyl]-morpholine (Intermediate 4)

Prepared analogously to the S isomer in Preparation 3 starting with the antipodal morpholine in Step a of Preparation 1.

Preparation 5

(2S) 2-[[4-(4-Chloro-2-methylphenoxy)-1-piperidinyl]methyl]-morpholine (Intermediate 5)

Prepared analogously to the S isomer in Preparation 1 starting with the appropriate phenoxypiperidine (WO 01/77101) in Step a of Preparation 1.

$^1$H NMR (CDCl$_3$) 1.70 (4H, s), 1.86 (2H, dd), 1.96 (2H, dd), 2.19 (3H, s), 2.35-2.45 (2H, m), 2.67-2.77 (2H, m), 2.80-2.96 (2H, m), 3.58-3.69 (2H, m), 3.85-3.92 (1H, m), 4.26-4.34 (1H, m), 6.73 (1H, d), 7.08 (2H, td).

Preparation 6

(2R) 2-[[4-(4-Chloro-2-methylphenoxy)-1-piperidinyl]methyl]-morpholine (Intermediate 6)

Prepared analogously to the S isomer in Preparation 5 starting with the antipodal morpholine in Step a of Preparation 1.

Preparation 7

4-(3,4-Dichlorophenoxy)-1-(3-piperidinylmethyl)-piperidine (Intermediate 7)

Step a: 1,1-Dimethylethyl 3-[[4-(3,4-dichlorophenoxy)-1-piperidinyl]methyl]-1-piperidinecarboxylate 4-(3,4-Dichlorophenoxy)piperidine (1 g) and 1,1-dimethylethyl 3-formyl-1-piperidinecarboxylate (Bioorg. Med. Chem. Lett., 1998, 8, 1595) were combined in tetrahydrofuran (4 ml) at 0° C., acetic acid (0.25 ml) was added and the mixture was stirred for 10 min, then at RT for 5 min. Sodium triacetoxyborohydride (1.25 g) was added in two portions and the resulting mixture was stirred for 16 h. Sodium hydroxide solution (2M) was added to neutralize the acid. The mixture was extracted with diethyl ether, the extracts were dried, filtered and evaporated to give an oil which was chromatographed eluting with dichloromethane:methanol:aqueous ammonia (97:2:1) to give the subtitle compound (1.63 g).

MS [M+H]$^+$ (ES+) 443

$^1$H NMR δ(CDCl$_3$) 1.05-1.14 (1H, m), 1.46 (11H, s), 1.61-1.66 (2H, m), 1.76-1.81 (3H, m), 1.92-1.98 (2H, m), 2.11-2.29 (4H, m), 2.62-2.81 (3H, m), 3.90-4.04 (2H, m), 4.21-4.27 (1H, m), 6.75 (1H, dd), 6.99 (1H, d), 7.30 (1H, d)

Step b: 4-(3,4-Dichlorophenoxy)-1-(piperidin-3-ylmethyl)piperidine 1,1-Dimethylethyl 3-[[4-(3,4-dichlorophenoxy)-1-piperidinyl]methyl]-1-piperidinecarboxylate (1.63 g) was dissolved in dichloromethane (30 ml) and trifluoroacetic acid (10 ml) was added. The mixture was stirred for 3 h, then concentrated. The residue was neutralized with sodium hydroxide solution (2M) and extracted with ethyl acetate thrice. The extracts were dried, filtered and evaporated to give the title compound (1.06 g).

$^1$H NMR δ(CDCl$_3$) 0.99-1.08 (1H, m), 1.45-1.56 (1H, m), 1.67-1.84 (5H, m), 1.94 (2H, s), 2.10-2.35 (6H, m), 2.54-2.71 (3H, m), 3.05 (1H, d), 3.19 (1H, d), 4.22-4.26 (1H, m), 6.73-6.77 (1H, m), 6.98-7.00 (1H, m), 7.27-7.32 (1H, m)

EXAMPLES 1 & 2

This Example illustrates the preparation of (α$^4$S,2R)-2-[[4-(3,4-dichlorophenoxy)-1-piperidinyl]methyl]-α-phenyl-4-morpholineacetic acid and (α$^4$R,2R)-2-[[4-(3,4-dichlorophenoxy)-1-piperidinyl]methyl]-α-phenylmorpholineacetic acid.

To a solution of (2S) 2-[[4-(3,4-dichlorophenoxy)-1-piperidinyl]methyl]-morpholine (0.300 g) in acetonitrile (3 ml) was added phenylboronic acid (0.106 g) and oxoacetic acid (0.08 ml). The mixture was heated for 4 minutes at 120° C. using microwaves at 50 Watts. The solvent was removed by evaporation and the product as two diastereoisomers was purified using reverse phase HPLC (25% MeCN/75% NH$_3$ aq (0.1%)) to give the title compounds as white solids (0.048 g and 0.044 g).

Faster Eluting Isomer

MS: ES(+ve): 479 (M+H)

$^1$H NMR (CDCl$_3$) δ 1.67-1.74 (3H, m), 1.83-1.97 (2H, m), 2.08-2.18 (1H, m), 2.44-2.51 (1H, m), 2.73-2.88 (4H, m), 2.91-3.03 (2H, m), 3.30-3.37 (1H, m), 3.64-3.74 (2H, m), 3.76-3.80 (1H, m), 4.08-4.20 (2H, m), 6.62-6.67 (1H, m), 6.87-6.91 (1H, m), 7.21-7.34 (4H, m), 7.49-7.56 (2H, m).

Slower Eluting Isomer

MS: ES(+ve): 479 (M+H)

$^1$H NMR (CDCl$_3$) δ 1.72-1.85 (3H, m), 1.87-1.98 (3H, m), 2.37-2.48 (2H, m), 2.57-2.65 (3H, m), 2.68-2.85 (4H, m), 3.70-3.80 (1H, m), 3.95-4.04 (2H, m), 4.20-4.29 (1H, m), 6.65-6.72 (1H, m), 6.90-6.95 (1H, m), 7.23-7.33 (4H, m), 7.30-7.44 (2H, m)

EXAMPLES 3 & 4

This Example illustrates the preparation of (α$^4$S,2S)-2-[[4-(3,4-dichlorophenoxy)-1-piperidinyl]methyl]-α-phenyl-4-morpholineacetic acid and (2S)-((2S)-2-{[4-(3,4-dichlorophenoxy)piperidin-1-yl]methyl}morpholin-4-yl)(phenyl) acetic acid (α$^4$R,2S)-2-[[4-(3,4-dichlorophenoxy)-1-piperidinyl]methyl]-α-phenyl-4-morpholineacetic acid.

To a solution of (2R) 2-[[4-(3,4-dichlorophenoxy)-1-piperidinyl]methyl]-morpholine (0.345 g) in acetonitrile (3 ml) was added phenylboronic acid (0.122 g) and oxoacetic acid (0.3 ml). The mixture was heated for 5 minutes at 100° C. using microwaves at 50 Watts. The solvent was removed by evaporation and the product as two diastereoisomers was purified using reverse phase HPLC (25% MeCN/75% NH$_3$ aq (0.1%)) to give the title compounds as white solids (0.048 g and 0.044 g).

Faster Eluting Isomer

MS: ES(+ve): 479 (M+H)

$^1$H NMR δ(CD$_3$OD) 1.25-1.35 (1H, m), 1.70-1.81 (2H, m), 1.95-2.03 (2H, m), 2.32 (2H, dd), 2.36-2.44 (3H, m), 2.52 (1H, d), 2.72-2.86 (2H, m), 3.09-3.18 (1H, m), 3.58-3.62 (1H, m), 3.61-3.68 (2H, m), 3.68-3.75 (1H, m), 3.87-3.97 (1H, m), 4.32-4.43 (1H, m), 6.88 (1H, dd), 7.09 (1H, d), 7.21-7.30 (3H, m), 7.37 (1H, d), 7.52 )2H, d).

Slower Eluting Isomer

MS: ES(+ve): 479 (M+H)

$^1$H NMR δ(CD$_3$OD) 1.29-1.38 (1H, m), 1.64 (1H, t), 1.69-1.79 (2H, m), 1.92-2.00 (2H, m), 2.17 (1H, dd), 2.22 (1H, dd), 2.32-2.39 (1H, m), 2.43 (1H, dd), 2.52 (1H, d), 2.68-2.78 (2H, m), 3.13 (1H, d), 3.65 (1H, s), 3.74-3.81 (1H, m), 3.82-3.89 (2H, m), 4.32-4.42 (1H, m), 6.89 (1H, dd), 7.09 (1H, d), 7.25-7.35 (3H, m), 7.39 (1H, d), 7.56 (2H, d).

EXAMPLES 5 AND 6

This Example illustrates the preparation of 3-[[4-(3,4-dichlorophenoxy)-1-piperidinyl]methyl]-alpha-phenyl-1-piperidineacetic acid.

To a solution of 4-(3,4-dichlorophenoxy)-1-(piperidin-3-ylmethyl)piperidine (1.0 g) in ethanol (5 ml) was added phenylboronic acid (0.36 g) and oxoacetic acid (0.45 ml 50% solution in water). The mixture was heated to 100° C. for 6 minutes using microwaves at 50 Watts. The crude reaction mixture was diluted with methanol and purified by reverse phase HPLC eluting with an acetonitrile ammonium acetate mixture. Gradient from 75% aqueous/25% acetonitrile to 5% aqueous/95% acetonitrile. This gave a mixture of diastereoisomers which were separated by reverse phase HPLC eluting with an acetonitrile ammonium acetate mixture. Gradient from 95% aqueous/5% acetonitrile to 50% aqueous/50% acetonitrile.

First Eluting Diastereoisomer

MS: APCI(+ve): 477 (M+H)

$^1$H NMR δ (CD$_3$OD plus 1 drop NaOD) 1.53-1.63 (2H, m), 1.69-1.85 (5H, m), 1.90-2.08 (4H, m), 2.18-2.38 (4H, m), 2.58-2.80 (3H, m), 3.18-3.27 (1H, m), 3.64 (1H, s), 4.33-4.46 (1H, m), 6.89 (1H, dd), 7.09 (1H, d), 7.20-7.30 (3H, m), 7.38 (1H, d), 7.54 (2H, d).

Second Eluting Diastereoisomer

MS: APCI(+ve): 477 (M+H)

$^1$H NMR δ (CD$_3$OD plus 1 drop NaOD) 1.31-1.42 (1H, m), 1.56-2.25 (14H, m), 2.52-2.67 (2H, m), 2.76-2.83 (1H, m), 3.19-3.25 (1H, m), 3.64 (1H, s), 4.26-4.37 (1H, m), 6.83-6.88 (1H, m), 7.05 (1H, d), 7.22-7.32 (3H, m), 7.37 (1H, d), 7.53 (2H, d).

EXAMPLES 7-12

Were Prepared by Similar Methods to Examples 1-6 Using the Apropriate Intermediate (Preparations 2-6)

| Example | Name | $^1$H NMR | M + H |
|---|---|---|---|
| 7 | 2-[[4-(4-chloro-2-methylphenoxy)-1-piperidinyl]methyl]-alpha-phenyl-, (2R)-4-morpholineacetic acid | δ(CDCl$_3$)1.80-2.01 (4H, m), 2.08-2.18 (2H, m), 2.15(3H, s), 2.42-2.51(1H, m), 2.62-2.71(1H, m), 2.74-3.07(4H, m), 3.08-3.31(2H, m), 3.64-3.81(3H, m), 4.04-4.10(1H, m), 4.15-4.24(1H, m), 4.26-4.34(1H, m), 6.62(1H, dd), 7.06 (1H, dd), 7.10(1H, d), 7.22-7.33(3H, m), 7.41(1H, d), 7.50-7.53(1H, m) | 459/461 |
| 8 | 2-[[4-(4-chloro-2-methylphenoxy)-1-piperidinyl]methyl]-alpha-phenyl-, (2S)-4-morpholineacetic acid | δ(CDCl$_3$)1.80-2.00 (4H, m), 2.07-2.19 (2H, m), 2.15(3H, s), 2.41-2.54(1H, m), 2.60-3.31(6H, m), 3.65-3.79(3H, m), 4.02-4.11(1H, m), 4.15-4.24(1H, m), 4.26-4.34(1H, m), 6.62(1H, t), 7.06 (1H, dd), 7.10(1H, d), 7.22-7.34(3H, m), 7.39-7.44(1H, m), 7.49-7.55(1H, m) | 459/461 |
| 9 | 2-[[4-(2,4-dichloro-3-methylphenoxy)-1-piperidinyl]methyl]-alpha-phenyl-, (2R)-4-morpholineacetic acid | δ(CDCl$_3$)1.59-2.01 (5H, m), 2.19(1H, t), 2.41-2.51(4H, m), 2.89-3.03(4H, m), 3.17-3.30(2H, m), 3.34-3.42(2H, m), 3.68-3.80(2H, m), 4.17-4.32(2H, m), 6.60(1H, d), 7.17 (1H, d), 7.21-7.33 (3H, m), 7.50-7.56 (2H, m) | 493/495 |
| 10 | 2-[[4-(2,4-dichloro-3-methylphenoxy)-1-piperidinyl]methyl]-alpha-phenyl-, (2R)-4-morpholineacetic acid | δ(CDCl$_3$)1.78-2.07 (5H, m), 2.30-2.41 (1H, m), 2.45(3H, s), 2.56-2.89(4H, m), 3.03-3.42(4H, m), 3.66-3.79(2H, m), 3.92-4.05(2H, m), 4.34(1H, s), 6.67 (1H, d), 7.18(1H, d), 7.21-7.27(3H, m), 7.36-7.43(2H, m) | 493/495 |

-continued

| Example | Name | $^1$H NMR | M + H |
|---|---|---|---|
| 11 | 2-[[4-(2,4-dichloro-3-methylphenoxy)-1-piperidinyl]methyl]-alpha-phenyl-, (2S)-4-morpholineacetic acid | δ(CDCl$_3$)1.70-1.83 (2H, m), 1.88-1.99 (2H, m), 2.19(1H, t), 2.42-2.52(4H, m), 2.90-3.00(4H, m), 3.13-3.47(5H, m), 3.69-3.78(3H, m), 4.19-4.31(2H, m), 6.59(1H, d), 7.17 (1H, d), 7.23-7.33 (3H, m), 7.55(2H,d) | 493/495 |
| 12 | 2-[[4-(2,4-dichloro-3-methylphenoxy)-1-piperidinyl]methyl]-alpha-phenyl-, (2S)-4-morpholineacetic acid | δ(CDCl$_3$)1.80-2.07 (4H, m), 2.14-2.14 (1H, m), 2.41-2.52 (3H, m), 2.66-3.54 (10H, m), 3.67-3.79 (2H, m), 4.04-4.14 (2H, m), 4.34-4.43 (1H, m), 6.66(1H, d), 7.19(1H, d), 7.24-7.31(4H, m), 7.39-7.45(1H, m) | 493/495 |

EXAMPLE 13

This Example illustrates the preparation of 2-[[(2R)-2-[[4-(3,4-dichlorophenoxy)-1-piperidinyl]methyl]-4-morpholinyl]methyl]-benzoic acid 2-[[4-(3,4-Dichlorophenoxy)-1-piperidinyl]methyl]-(2S)-morpholine (0.58 g), 2-carboxybenzaldehyde (0.30 g) and acetic acid (0.5 ml) were added to tetrahydrofuran (3 ml) and stirred at room temperature for 5 min. The reaction mixture was then treated with sodium triacetoxyborohydride (0.53 g) and stirring continued overnight. The crude reaction mixture was filtered, diluted with methanol (1 ml) and purified by reverse phase HPLC (eluents 0.1% aqueous ammonium acetate and acetonitrile, gradient, 95% aqueous-50% aqueous) to give the title compound as a white solid (0.15 g).

MS [M−H]$^−$ (ES−) 477/479

$^1$H NMR δ(CD$_3$OD) 1.59-1.73 (2H, m), 1.74-1.93 (3H, m), 2.08(1H, d), 2.18-2.42 (4H, m), 2.57-2.71 (4H, m), 3.54 (1H, d), 3.62-3.74 (4H, m), 4.23-4.32 (1H, m), 6.78 (1H, dd), 6.98 (1H, d), 7.08-7.19 (2H, m), 7.26-7.36 (3H, m)

EXAMPLE 14

This Example illustrates the preparation of methyl 2-[(2R)-2-[[4-(3,4-dichlorophenoxy)-1-piperidinyl]methyl]-4-morpholinyl]-benzoate 2-[[4-(3,4-Dichlorophenoxy)-1-piperidinyl]methyl]-(2S)-morpholine (0.2 g), methyl 2-fluorobenzoate (0.09 g) and potassium carbonate (0.12 g) were added to dimethylformamide (1 ml) and the mixture was heated at 100° C. overnight. The reaction mixture was poured into water and product was extracted with ethyl acetate. The ethyl acetate was washed with brine; dried (MgSO$_4$), filtered and concentrated by evaporation under reduced pressure to give crude product This was purified by flash chromatography, eluting with 2% methanol, 0.1% triethylamine in dichloromethane to give the title compound (0.06 g).

MS [M+H]$^+$ (ES+) 477/479

EXAMPLE 15

This Example illustrates the preparation of 2-[(2R)-2-[[4-(3,4-dichlorophenoxy)-1-piperidinyl]methyl]-4-morpholinyl]-benzoic acid 2-[(2R)-2-[[4-(3,4-Dichlorophenoxy)-1-piperidinyl]methyl]-4-morpholinyl]-methyl benzoate (0.06 g) was dissolved in tetrahydrofuran (1 ml) and treated with potassium trimethylsilanolate (0.02 g). The reaction mixture was stirred at room temperature overnight. The crude reaction mixture was diluted with methanol (1 ml), acidified to pH 5 by addition of acetic acid and purified by reverse phase HPLC (eluents 0.1% aqueous ammonium acetate and acetonitrile, gradient, 95% aqueous-5% aqueous) to give the title compound as a white solid (0.02 g).

MS [M−H]$^−$ (ES−) 463/465

$^1$H NMR δ(CD$_3$OD) 1.73-1.85 (2H, m), 1.91-2.04 (2H, m), 2.56-2.76 (5H, m), 2.86-2.96 (3H, m), 3.04-3.18 (2H, m), 3.76 (1H, td), 3.87-3.96 (2H, m), 4.35-4.44 (1H, m), 6.81 (1H, dd), 7.01-7.07 (2H, m), 7.13 (1H, d), 7.27-7.34 (2H, m), 7.58 (1H, dd)

EXAMPLES 16-55

Are Examples of Compounds of Formula (I) and were Prepared by the Following General Method To a solution of (2R)-2-{[4-(3,4-dichlorophenoxy)piperidin-1-yl]methyl}morpholine or (2S)-2-{[4-(3,4-dichlorophenoxy)piperidin-1-yl]methyl}morpholine as appropriate (2.8 mg) in dimethylacetamide (0.05 ml) was added the appropriate boronic acid (1 molar equivalent in 0.07 ml dimethylacetamide) and oxoacetic acid (1 molar equivalent of a 50% aqueous solution in 0.01 ml dimethylacetamide). The mixture was heated to 100° C. for 6 minutes using microwaves at 300 Watts. Purification using reverse phase HPLC (with a gradient 0.1% aqueous formic acid:acetonitrile 90:10 to 35:65) gave the compounds of Examples 16-55.

| Example | Name | (M + H)$^+$ |
|---|---|---|
| 16 | (2S)-2-[[4-(3,4-dichlorophenoxy)-1-piperidinyl]-methyl]-α-(6-methoxy-2-naphthalenyl)-4-morpholineacetic acid | 559 |
| 17 | (2S)-2-[[4-(3,4-dichlorophenoxy)-1-piperidinyl]-methyl]-α-(4-methoxyphenyl)-4-morpholineacetic acid | 509 |
| 18 | (2S)-2-[[4-(3,4-dichlorophenoxy)-1-piperidinyl]-methyl]-α-(4-methylphenyl)-4-morpholineacetic acid | 493 |
| 19 | (2S)-2-[[4-(3,4-dichlorophenoxy)-1-piperidinyl]-methyl]-α-(2-thienyl)-4-morpholineacetic acid | 485 |
| 20 | (2S)-2-[[4-(3,4-dichlorophenoxy)-1-piperidinyl]-methyl]-α-(3-thienyl)-4-morpholineacetic acid | 485 |
| 21 | (2S)-α-(2-benzofuranyl)-2-[[4-(3,4-dichlorophenoxy)-1-piperidinyl]methyl]-4-morpholineacetic acid | 519 |
| 22 | (2S)-2-[[4-(3,4-dichlorophenoxy)-1-piperidinyl]-methyl]-α-(2-methoxyphenyl)-4-morpholineacetic acid | 509 |
| 23 | (2S)-2-[[4-(3,4-dichlorophenoxy)-1-piperidinyl]-methyl]-α-(3-fluoro-4-propoxyphenyl)-4-morpholineacetic acid | 555 |
| 24 | (2S)-2-[[4-(3,4-dichlorophenoxy)-1-piperidinyl]-methyl]-α-[4-(1,1-dimethylethoxy)phenyl]-4-morpholineacetic acid | 551 |
| 25 | (2S)-2-[[4-(3,4-dichlorophenoxy)-1-piperidinyl]-methyl]-α-[4-(phenylmethoxy)phenyl]-4-morpholineacetic acid | 585 |
| 26 | (2S)-2-[[4-(3,4-dichlorophenoxy)-1-piperidinyl]-methyl]-α-(5-methyl-2-furanyl)-4-morpholineacetic acid | 483 |
| 27 | (2S)-2-[[4-(3,4-dichlorophenoxy)-1-piperidinyl]-methyl]-α-(2,3,4-trimethoxyphenyl)-4-morpholineacetic acid | 569 |

-continued

| Example | Name | (M + H)+ |
|---|---|---|
| 28 | (2S)-2-[[4-(3,4-dichlorophenoxy)-1-piperidinyl]-methyl]-α-(2,6-dimethoxyphenyl)-4-morpholineacetic acid | 539 |
| 29 | (2S)-2-[[4-(3,4-dichlorophenoxy)-1-piperidinyl]-methyl]-α-(3,4-dimethoxyphenyl)-4-morpholineacetic acid | 539 |
| 30 | (2S)-2-[[4-(3,4-dichlorophenoxy)-1-piperidinyl]-methyl]-α-(2-furanyl)-4-morpholineacetic acid | 469 |
| 31 | (2S)-2-[[4-(3,4-dichlorophenoxy)-1-piperidinyl]-methyl]-α-(2,4-dimethoxyphenyl)-4-morpholineacetic acid | 539 |
| 32 | (2S)-2-[[4-(3,4-dichlorophenoxy)-1-piperidinyl]-methyl]-α-(4-ethylphenyl)-4-morpholineacetic acid | 507 |
| 33 | (2S)-2-[[4-(3,4-dichlorophenoxy)-1-piperidinyl]-methyl]-α-(4-hydroxyphenyl)-4-morpholineacetic acid | 495 |
| 34 | (2S)-2-[[4-(3,4-dichlorophenoxy)-1-piperidinyl]-methyl]-α-[4-(1,1-dimethylethyl)phenyl]-4-morpholineacetic acid | 535 |
| 35 | (2S)-α-[4-(9H-carbazol-9-ylmethyl)phenyl]-2-[[4-(3,4-dichlorophenoxy)-1-piperidinyl]methyl]-4-morpholineacetic acid | 658 |
| 36 | (2R)-2-[[4-(3,4-dichlorophenoxy)-1-piperidinyl]-methyl]-α-(6-methoxy-2-naphthalenyl)-4-morpholineacetic acid | 559 |
| 37 | (2R)-2-[[4-(3,4-dichlorophenoxy)-1-piperidinyl]-methyl]-α-(4-methoxyphenyl)-4-morpholineacetic acid | 509 |
| 38 | (2R)-2-[[4-(3,4-dichlorophenoxy)-1-piperidinyl]-methyl]-α-(4-methylphenyl)-4-morpholineacetic acid | 493 |
| 39 | (2R)-2-[[4-(3,4-dichlorophenoxy)-1-piperidinyl]-methyl]-α-(2-thienyl)-4-morpholineacetic acid | 485 |
| 40 | (2R)-2-[[4-(3,4-dichlorophenoxy)-1-piperidinyl]-methyl]-α-(3-thienyl)-4-morpholineacetic acid | 485 |
| 41 | (2R)-α-(2-benzofuranyl)-2-[[4-(3,4-dichlorophenoxy)-1-piperidinyl]methyl]-4-morpholineacetic acid | 519 |
| 42 | (2R)-2-[[4-(3,4-dichlorophenoxy)-1-piperidinyl]-methyl]-α-(2-methoxyphenyl)-4-morpholineacetic acid | 509 |
| 43 | (2R)-2-[[4-(3,4-dichlorophenoxy)-1-piperidinyl]-methyl]-αa-(3-fluoro-4-propoxyphenyl)-4-morpholineacetic acid | 555 |
| 44 | (2R)-2-[[4-(3,4-dichlorophenoxy)-1-piperidinyl]-methyl]-α-[4-(1,1-dimethylethoxy)phenyl]-4-morpholineacetic acid | 551 |
| 45 | (2R)-2-[[4-(3,4-dichlorophenoxy)-1-piperidinyl]-methyl]-α-[4-(phenylmethoxy)phenyl]-4-morpholineacetic acid | 585 |
| 46 | (2R)-2-[[4-(3,4-dichlorophenoxy)-1-piperidinyl]-methyl]-α-(5-methyl-2-furanyl)-4-morpholineacetic acid | 483 |
| 47 | (2R)-2-[[4-(3,4-dichlorophenoxy)-1-piperidinyl]-methyl]-α-(2,3-trimethoxyphenyl)-4-morpholineacetic acid | 569 |
| 48 | (2R)-2-[[4-(3,4-dichlorophenoxy)-1-piperidinyl]-methyl]-α-(2,6-dimethoxyphenyl)-4-morpholineacetic acid | 539 |
| 49 | (2R)-2-[[4-(3,4-dichlorophenoxy)-1-piperidinyl]-methyl]-α-(3,4-dimethoxyphenyl)-4-morpholineacetic acid | 539 |
| 50 | (2R)-2-[[4-(3,4-dichlorophenoxy)-1-piperidinyl]-methyl]-α-(2-furanyl)-4-morpholineacetic acid | 469 |
| 51 | (2R)-2-[[4-(3,4-dichlorophenoxy)-1-piperidinyl]-methyl]-α-(2,4-dimethoxyphenyl)-4-morpholineacetic acid | 539 |
| 52 | (2R)-2-[[4-(3,4-dichlorophenoxy)-1-piperidinyl]-methyl]-α-(4-ethylphenyl)-4-morpholineacetic acid | 507 |
| 53 | (2R)-2-[[4-(3,4-dichlorophenoxy)-1-piperidinyl]-methyl]-α-(4-hydroxyphenyl)-4-morpholineacetic acid | 495 |
| 54 | (2R)-2-[[4-(3,4-dichlorophenoxy)-1-piperidinyl]-methyl]-α-[4-(1,1-dimethylethyl)phenyl]-4-morpholineacetic acid | 535 |
| 55 | (2R)-α-[4-(9H-carbazol-9-ylmethyl)phenyl]-2-[[4-(3,4-dichlorophenoxy)-1-piperidinyl]methyl]-4-morpholineacetic acid | 658 |

EXAMPLE 56

Pharmacological Analysis: Calcium Flux $[Ca^{2+}]_i$ Assay

Human Eosinophils

Human eosinophils were isolated from EDTA anticoagulated peripheral blood as previously described (Hansel et al., J. Immunol. Methods, 1991, 145, 105-110). The cells were resuspended ($5 \times 10^6$ ml$^{-1}$) and loaded with 5 μM FLUO-3/AM+Pluronic F127 2.2 μl/ml (Molecular Probes) in low potassium solution (LKS; NaCl 118 mM, MgSO$_4$ 0.8 mM, glucose 5.5 mM, Na$_2$CO$_3$ 8.5 mM, KCl 5 mM, HEPES 20 mM, CaCl$_2$ 1.8 mM, BSA 0.1%, pH 7.4) for one hour at room temperature. After loading, cells were centrifuged at 200 g for 5 min and resuspended in LKS at $2.5 \times 10^6$ ml$^{-1}$. The cells were then transferred to 96 well FLIPr plates (Poly-D-Lysine plates from Becton Dickinson pre-incubated with 5 μM fibronectin for two hours) at 25 μl/well. The plate was centrifuged at 200 g for 5 min and the cells were washed twice with LKS (200 μl; room temperature).

A compound of the Examples was pre-dissolved in DMSO and added to a final concentration of 0.1% (v/v) DMSO. Assays were initiated by the addition of an A$_{50}$ concentration of eotaxin and the transient increase in fluo-3 fluorescence ($1_{Ex}$=490 nm and $1_{Em}$=520 nm) monitored using a FLIPR (Fluorometric Imaging Plate Reader, Molecular Devices, Sunnyvale, U.S.A.).

EXAMPLE 57

Human Eosinophil Chemotaxis

Human eosinophils were isolated from EDTA anticoagulated peripheral blood as previously described (Hansel et al., J. Immunol. Methods, 1991, 145, 105-110). The cells were resuspended at $10 \times 10^6$ ml$^{-1}$ in RPMI containing 200 IU/ml penicillin, 200 μg/ml streptomycin sulphate and supplemented with 10% HIFCS, at room temperature.

Eosinophils (700 μl) were pre-incubated for 15 mins at 37° C. with 7 μl of either vehicle or compound (100× required final concentration in 10% DMSO). The chemotaxis plate (ChemoTx, 3 μm pore, Neuroprobe) was loaded by adding 28 μl of a concentration of eotaxin (0.1 to 100 nM) containing a concentration of a compound according to the Examples or solvent to the lower wells of the chemotaxis plate. The filter was then placed over the wells and 25 μl of eosinophil suspension were added to the top of the filter. The plate was incubated for 1 hr at 37° C. in a humidified incubator with a 95% air/5% CO$_2$ atmosphere to allow chemotaxis.

The medium, containing cells that had not migrated, was carefully aspirated from above the filter and discarded. The filter was washed once with phosphate buffered saline (PBS) containing 5 mM EDTA to remove any adherent cells. Cells that had migrated through the filter were pelleted by centrifugation (300×g for 5 mins at room temperature) and the filter removed and the supernatant transferred to each well of a 96-well plate (Costar). The pelleted cells were lysed by the addition of 28 μl of PBS containing 0.5% Triton x100 followed by two cycles of freeze/thawing. The cell lysate was then added to the supernatant. The number of eosinophils migrating was quantified according to the method of Strath et al., *J. Immunol. Methods*, 1985, 83, 209 by measuring eosinophil peroxidase activity in the supernatant.

Compounds of the Examples were found to be antagonists of the eotaxin mediated human eosinophil chemotaxis.

| Example | % Inhibition (3 nM Human Eotaxin) |
|---|---|
| 2 | 96.4 |
| 5 | 96.9 |

EXAMPLE 58

Guinea-Pig Isolated Trachea (See for example, Harrison, R. W. S., Carswell, H. & Young, J. M. (1984) European, J. Pharmacol., 106, 405-409.)

Male albino Dunkin-Hartley guinea-pigs (250 g) were killed by cervical dislocation and the whole trachea removed. After clearing the adherent connective tissue, the trachea was cut into six ring segments each three cartilage bands wide and then suspended in 20 ml organ baths containing Krebs-Henseleit solution of the following composition (mM): NaCl 117.6, $NaH_2PO_4$ 0.9, $NaHCO_3$ 25.0, $MgSO_4$ 1.2, KCl 5.4, $CaCl_2$ 2.6 and glucose 11.1. The buffer was maintained at 37° C. and gassed with 5% $CO_2$ in oxygen. Indomethacin (2.8 μM) was added to the Krebs solution to prevent development of smooth muscle tone due to the synthesis of cyclo-oxygenase products. The tracheal rings were suspended between two parallel tungsten wire hooks, one attached to an Ormed beam isometric force transducer and the other to a stationary support in the organ bath. Changes in isometric force were recorded on 2-channel Sekonic flat bed chart recorders.

Experimental Protocols

At the beginning of each experiment a force of 1 g was applied to the tissues and this was reinstated over a 60 minute equilibration period until a steady resting tone was achieved. Subsequently, a cumulative histamine concentration effect (E/[A]) curve was constructed at 0.5 $\log_{10}$ unit increments, in each tissue. The tissues were then washed and approximately 30 minutes later, test compound or vehicle (20% DMSO) was, added. Following an incubation period of 60 minutes a second E/[A] curve was performed to histamine.

Contraction responses were recorded as a percentage of the first curve maximum.

Data Analysis

Experimental E/[A] curve data were analyzed for the purposes of estimating the potencies ($pA_{50}$ values) of histamine in the absence and presence of the test compound. Affinity ($pA_2$) values of test compounds were subsequently calculated using the following equation:

$$\log(r-1) = \log [B] + pA_2$$

where r=$[A]_{50}$ in presence of test compound/$[A]_{50}$ in absence of antagonist and [B] is the concentration of test compound. Compounds of the Examples were found to be H1 antagonists.

EXAMPLE 59

Histamine H1 receptor binding activity of compounds of the invention was assessed by competition displacement of 1 nM [3H]-pyrilamine (Amersham, Bucks, Product code TRK 608, specific activity 30 Ci/mmol) to 2 μg membranes prepared from recombinant CHO-1 cells expressing the human H1 receptor (Euroscreen SA, Brussels, Belgium, product code ES-390-M) in assay buffer (50 mM Tris pH 7.4 containing 2 mM $MgCl_2$, 250 mM sucrose and 100 mM NaCl) for 1 hour at room temperature.

The following compounds of the invention gave inhibition of [3H] pyrilimine binding:

| Example | H1 antagonism pKi |
|---|---|
| 1 | 7.1 |
| 2 | 6.9 |
| 5 | 7.2 |
| 6 | 7.3 |
| 7 | 6.2 |
| 8 | 6.9 |
| 9 | 6.5 |
| 10 | 6.1 |
| 11 | 6.6 |
| 12 | 7.5 |
| 13 | 7.5 |
| 15 | 7.6 |

The invention claimed is:
1. A compound of formula (I):

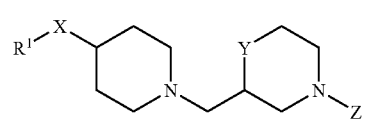

wherein:
Z is

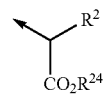

n is 0 or 1;
X is O;
Y is $CH_2$;
$R^1$ is aryl;
$R^2$ is $C_{3-7}$ cycloalkyl {optionally substituted by $C_{1-4}$ alkyl, aryl or oxo}, $C_{3-7}$ cycloalkenyl {optionally substituted by oxo, $C_{1-6}$ alkyl or aryl}, aryl or heterocyclyl; wherein the foregoing aryl and heterocyclyl moieties are optionally substituted by: halogen, cyano, nitro, hydroxy, oxo, $S(O)_pR^4$, $OC(O)NR^5R^6$, $NR^7R^8$, $NR^9C(O)R^{10}$, $NR^{11}C(O)NR^{12}R^{13}$, $S(O)_2NR^{14}R^{15}$, $NR^{16}S(O)_2R^{17}$, $C(O)NR^{18}R^{19}$, $C(O)R^{20}$, $CO_2R^{21}$, $NR^{22}CO_2R^{23}$, $C_{1-6}$ alkyl, $C_{1-6}$ haloalkyl, $C_{1-6}$ alkoxy($C_{1-6}$)alkyl, $C_{1-6}$ alkoxy, $C_{1-6}$ haloalkoxy, $C_{1-6}$ alkoxy($C_{1-6}$)alkoxy, $C_{1-6}$ alkylthio, $C_{1-6}$ haloalkylthio, $C_{2-6}$ alkenyl, $C_{2-6}$ alkynyl, $C_{3-10}$ cycloalkyl (optionally substituted by $C_{1-4}$ alkyl or oxo), methylenedioxy, difluoromethylenedioxy, phenyl, phenyl($C_{1-4}$)alkyl, phenoxy, phenylthio, phenyl($C_{1-4}$) alkoxy, heterocyclyl, heterocyclyl($C_{1-4}$)alkyl, heterocyclyloxy or heterocyclyl($C_{1-4}$) alkoxy; wherein any of the immediately foregoing phenyl and heterocyclyl moieties are optionally substituted with halogen, hydroxy, nitro, $S(O)_q(C_{1-4}$ alkyl), $S(O)_2NH_2$, cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$ (and these alkyl groups optionally being joined to form a ring as described for $R^5$ and $R^6$ below), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$;

M and T are, independently, hydrogen, halogen, cyano, nitro, hydroxy, oxo, $S(O)_pR^4$, $OC(O)NR^5R^6$, $NR^7R^8$, $NR^9C(O)R^{10}$, $NR^{11}C(O)NR^{12}R^{13}$, $S(O)_2NR^{14}R^{15}$, $NR^{16}S(O)_2R^{17}$, $C(O)NR^{18}R^{19}$, $C(O)R^{20}$, $CO_2R^{21}$, $NR^{22}CO_2R^{23}$, $C_{1-6}$ alkyl, $C_{1-6}$ haloalkyl, $C_{1-6}$ alkoxy ($C_{1-6}$)alkyl, $C_{1-6}$ alkoxy, $C_{1-6}$ haloalkoxy, $C_{1-6}$ alkoxy ($C_{1-6}$)alkoxy, $C_{1-6}$ alkylthio, $C_{1-6}$ haloalkylthio, $C_{2-6}$ alkenyl, $C_{2-6}$ alkynyl, $C_{3-10}$ cycloalkyl (optionally substituted by $C_{1-4}$ alkyl or oxo), methylenedioxy, difluoromethylenedioxy, phenyl, phenyl($C_{1-4}$)alkyl, phenoxy, phenylthio, phenyl($C_{1-4}$)alkoxy, heterocyclyl, heterocyclyl($C_{1-4}$)alkyl, heterocyclyloxy or heterocyclyl($C_{1-4}$)alkoxy; wherein any of the immediately foregoing phenyl and heterocyclyl moieties are optionally substituted with halogen, hydroxy, nitro, $S(O)_q(C_{1-4}$ alkyl), $S(O)_2NH_2$, cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$ (and these alkyl groups optionally being joined to form a ring as described for $R^5$ and $R^6$ below), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$;

p and q are, independently, 0, 1 or 2;

$R^3$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{18}$, $R^{19}$, $R^{20}$, $R^{21}$ and $R^{22}$ are, independently, hydrogen, $C_{1-6}$ alkyl (optionally substituted by halogen, hydroxy or $C_{3-10}$ cycloalkyl), $CH_2(C_{2-6}$ alkenyl), phenyl (optionally substituted by halogen, hydroxy, nitro, $NH_2$, $NH(C_{1-4}$ alkyl), $N(C_{1-4}$ alkyl)$_2$ (and these alkyl groups optionally being joined to form a ring as described for $R^5$ and $R^6$ below), $S(O)_2(C_{1-4}$ alkyl), $S(O)_2NH_2$, cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$ (and these alkyl groups optionally being joined to form a ring as described for $R^5$ and $R^6$ below), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$) or heterocyclyl (optionally substituted by halogen, hydroxy, nitro, $NH_2$, $NH(C_{1-4}$ alkyl), $N(C_{1-4}$ alkyl)$_2$ (and these alkyl groups optionally being joined to form a ring as described for $R^5$ and $R^6$ below), $S(O)_2(C_{1-4}$ alkyl), $S(O)_2NH_2$, $S(O)_2NH(C_{1-4}$ alkyl), $S(O)_2N(C_{1-4}$ alkyl)$_2$ (and these alkyl groups optionally being joined to form a ring as described for $R^5$ and $R^6$ below), cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$ (and these alkyl groups optionally being joined to form a ring as described for $R^5$ and $R^6$ below), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$);

alternatively $NR^5R^6$, $NR^7R^8$, $NR^{12}R^{13}$, $NR^{14}R^{15}$, or $NR^{18}R^{19}$, independently, form a 4-7 membered heterocyclic ring, azetidine, pyrrolidine, piperidine, azepine, 1,4-morpholine or 1,4-piperazine, the latter optionally substituted by $C_{1-4}$ alkyl on the distal nitrogen;

$R^4$, $R^{17}$ and $R^{23}$ are, independently, $C_{1-6}$ alkyl (optionally substituted by halogen, hydroxy or $C_{3-10}$ cycloalkyl), $CH_2(C_{2-6}$ alkenyl), phenyl (optionally substituted by halogen, hydroxy, nitro, $NH_2$, $NH(C_{1-4}$ alkyl), $N(C_{1-4}$ alkyl)$_2$ (and these alkyl groups optionally being joined to form a ring as described for $R^5$ and $R^6$ above), $S(O)_2(C_{1-4}$ alkyl), $S(O)_2NH_2$, $S(O)_2NH(C_{1-4}$ alkyl), $S(O)_2N(C_{1-4}$ alkyl)$_2$ (and these alkyl groups optionally being joined to form a ring as described for $R^5$ and $R^6$ above), cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$ (and these alkyl groups optionally being joined to form a ring as described for $R^5$ and $R^6$ above), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$) or heterocyclyl (optionally substituted by halogen, hydroxy, nitro, $NH_2$, $NH(C_{1-4}$ alkyl), $N(C_{1-4}$ alkyl)$_2$ (and these alkyl groups optionally being joined to form a ring as described for $R^5$ and $R^6$ above), $S(O)_2(C_{1-4}$ alkyl), $S(O)_2NH_2$, $S(O)_2NH(C_{1-4}$ alkyl), $S(O)_2N(C_{1-4}$ alkyl)$_2$ (and these alkyl groups optionally being joined to form a ring as described for $R^5$ and $R^6$ above), cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$ (and these alkyl groups optionally being joined to form a ring as described for $R^5$ and $R^6$ above), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$);

$R^{24}$ is hydrogen, $C_{1-6}$ alkyl or benzyl;

or an N-oxide thereof; or a pharmaceutically acceptable salt thereof.

2. A compound of formula (I) as claimed in claim 1 wherein $R^{24}$ is hydrogen.

3. A compound of formula (I) as claimed in claim 1 wherein $R^1$ is phenyl optionally substituted with fluorine, chlorine or $C_{1-4}$ alkyl.

4. A compound of formula (I) as claimed in claim 1 wherein $R^2$ is phenyl or heterocyclyl, either of which is optionally substituted by: halo, hydroxy, nitro, cyano, amino, $C_{1-4}$ alkyl (optionally substituted by $S(O)_2(C_{1-4}$ alkyl) or $S(O)_2$phenyl), $C_{1-4}$ alkoxy, $S(O)_pR^4$ (wherein p is 0, 1 or 2), $C(O)NH_2$, $NHS(O)_2(C_{1-4}$ alkyl), $S(O)_2NH_2$, $S(O)_2NH(C_{1-4}$ alkyl) or $S(O)_2N(C_{1-4}$ alkyl)$_2$; and $R^4$ is hydroxyalkyl, $C_{3-7}$ cycloalkyl or $C_{3-7}$ cycloalkyl($C_{1-4}$ alkyl).

5. A process for preparing a compound of formula (I) as claimed in claim 1, the process comprising:

A. when Z is $CHR^2CO_2R^{24}$:

i. coupling a compound of formula (II):

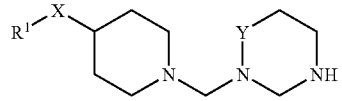

(II)

with a compound of formula (III):

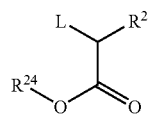

(III)

wherein L is a suitable leaving group, in a suitable solvent; or, ii. reductive amination of a compound (II) with an ester compound of formula (IIIa):

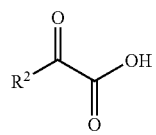

(IIIa)

in the presence of $NaBH(OAc)_3$ and acetic acid, followed optionally by removal of the ester group; or iii. a three component coupling of a compound of formula (II) with compounds of formula (IIIb) and (IIIc):

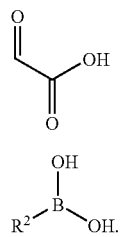

(IIIb)

(IIIc)

6. A pharmaceutical composition which comprises a compound of the formula (I), or a pharmaceutically acceptable salt thereof, as claimed in claim 1, and a pharmaceutically acceptable adjuvant, diluent or carrier.

* * * * *

UNITED STATES PATENT AND TRADEMARK OFFICE
CERTIFICATE OF CORRECTION

PATENT NO.        : 7,517,989 B2
APPLICATION NO.   : 10/508331
DATED             : April 14, 2009
INVENTOR(S)       : Christopher Luckhurst It is certified that error appears in the above-identified patent and that said Letters Patent is hereby corrected as shown below:

First Page, Column 2
Abstract, Line 5, delete "achemokine" and insert -- a chemokine --

Column 24
Line 34 (approx.), after " 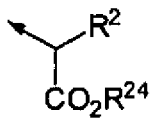 " insert -- ; --

Column 24
Line 55 (approx.), delete ""heterocyclyl($C_{1-4}$) alkoxy;" and insert
-- heterocyclyl($C_{1-4}$)alkoxy; --

Column 25
Line 7-8 (approx.), delete "heterocyclyl($C_{1-4}$) alkoxy;" and insert
-- heterocyclyl($C_{1-4}$)alkoxy; --

Column 26
Line 18 (approx.), delete "is" and insert -- is $C_{1-4}$ alkyl, $C_{1-4}$ --

UNITED STATES PATENT AND TRADEMARK OFFICE
CERTIFICATE OF CORRECTION

PATENT NO. : 7,517,989 B2
APPLICATION NO. : 10/508331
DATED : April 14, 2009
INVENTOR(S) : Christopher Luckhurst It is certified that error appears in the above-identified patent and that said Letters Patent is hereby corrected as shown below:

Column 26

Line 25 (approx.), delete "  " and insert -- 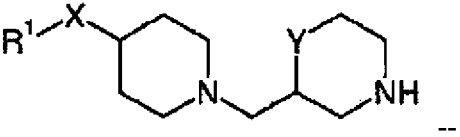 --

Signed and Sealed this

Twenty-sixth Day of May, 2009

JOHN DOLL
*Acting Director of the United States Patent and Trademark Office*